US011357468B2

(12) United States Patent
Lee et al.

(10) Patent No.: US 11,357,468 B2
(45) Date of Patent: Jun. 14, 2022

(54) CONTROL APPARATUS OPERATIVELY COUPLED WITH MEDICAL IMAGING APPARATUS AND MEDICAL IMAGING APPARATUS HAVING THE SAME

(71) Applicant: SAMSUNG ELECTRONICS CO., LTD., Suwon-si (KR)

(72) Inventors: Jong Kee Lee, Seoul (KR); Na Ri Kim, Seoul (KR); Olivia Lee, Seoul (KR); Ja Youn Lee, Seoul (KR); Yun Su Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 502 days.

(21) Appl. No.: 15/916,366

(22) Filed: Mar. 9, 2018

(65) Prior Publication Data

US 2018/0192984 A1    Jul. 12, 2018

Related U.S. Application Data

(63) Continuation of application No. 14/095,133, filed on Dec. 3, 2013, now abandoned.
(Continued)

(30) Foreign Application Priority Data

Mar. 27, 2013    (KR) .......................... 10-2013-0032576

(51) Int. Cl.
*A61B 6/00*    (2006.01)
*G01R 33/54*    (2006.01)
(Continued)

(52) U.S. Cl.
CPC ................ *A61B 6/54* (2013.01); *A61B 5/055* (2013.01); *A61B 5/748* (2013.01); *A61B 5/7445* (2013.01);
(Continued)

(58) Field of Classification Search
CPC ........... A61B 6/54; A61B 6/462; A61B 6/467; A61B 6/548; A61B 6/032; A61B 6/0407;
(Continued)

(56) References Cited

U.S. PATENT DOCUMENTS 5,687,717 A    11/1997 Halpern et al.
6,522,713 B1    2/2003 Valiga et al.
(Continued)

FOREIGN PATENT DOCUMENTS

EP    2389865 A1    11/2011
JP    2006187422 A    7/2006
(Continued)

OTHER PUBLICATIONS

Communication dated May 23, 2017, issued by the European Patent Office in counterpart European application No. 13194357.3.
(Continued)

*Primary Examiner* — Colin T. Sakamoto
(74) *Attorney, Agent, or Firm* — Sughrue Mion, PLLC

(57) ABSTRACT

The medical imaging apparatus includes a scanner configured to scan the object to image the internal area of the object; a patient table configured to convey the object to the scanner; an imager which is mounted on the scanner and configured to capture an image of the object on the patient table; and a mobile display device configured to display the image of the object captured by the imager.

17 Claims, 28 Drawing Sheets

Related U.S. Application Data

(60) Provisional application No. 61/732,633, filed on Dec. 3, 2012.

(51) Int. Cl.
    *G01R 33/28*     (2006.01)
    *A61B 5/055*     (2006.01)
    *A61B 5/00*     (2006.01)
    *A61B 6/03*     (2006.01)
    *A61B 6/04*     (2006.01)

(52) U.S. Cl.
CPC ............ *A61B 5/7475* (2013.01); *A61B 6/462* (2013.01); *A61B 6/467* (2013.01); *A61B 6/548* (2013.01); *G01R 33/283* (2013.01); *G01R 33/546* (2013.01); *A61B 6/032* (2013.01); *A61B 6/0407* (2013.01); *A61B 6/469* (2013.01); *A61B 6/56* (2013.01)

(58) Field of Classification Search
CPC ......... A61B 6/469; A61B 6/56; A61B 5/0555; A61B 5/7445; A61B 5/7475; A61B 5/748; G01R 33/283; G01R 33/546
See application file for complete search history.

(56) References Cited

U.S. PATENT DOCUMENTS

| | | | |
|---|---|---|---|
| 7,677,802 B2 | 3/2010 | Haras | |
| 7,869,562 B2 * | 1/2011 | Khamene | A61B 6/08 378/20 |
| 2002/0041654 A1 | 4/2002 | Hayashi | |
| 2003/0095697 A1 * | 5/2003 | Wood | A61B 6/037 382/131 |
| 2004/0082852 A1 * | 4/2004 | Cherek | A61B 6/08 600/427 |
| 2004/0160463 A1 | 8/2004 | Battles et al. | |
| 2005/0085710 A1 * | 4/2005 | Earnst | A61B 6/0487 600/411 |
| 2005/0288571 A1 * | 12/2005 | Perkins | A61B 50/13 600/407 |
| 2007/0189462 A1 | 8/2007 | Spahn | |
| 2008/0009696 A1 * | 1/2008 | Hempel | A61B 5/055 600/407 |
| 2008/0081992 A1 | 4/2008 | Kagermeier | |
| 2008/0089463 A1 | 4/2008 | Nakamura et al. | |
| 2008/0122796 A1 | 5/2008 | Jobs et al. | |
| 2008/0181359 A1 * | 7/2008 | Stayman | A61B 6/4405 378/20 |
| 2009/0160640 A1 | 6/2009 | Leung et al. | |
| 2010/0059679 A1 | 3/2010 | Albrecht | |
| 2010/0238620 A1 * | 9/2010 | Fish | G06F 1/1654 361/679.29 |
| 2011/0291800 A1 | 12/2011 | Butzine et al. | |
| 2011/0317816 A1 * | 12/2011 | Bechard | A61B 6/56 378/98.8 |
| 2013/0109371 A1 | 5/2013 | Brogan et al. | |
| 2013/0222318 A1 | 8/2013 | Gotman et al. | |
| 2013/0231567 A1 | 9/2013 | Barthe et al. | |
| 2015/0305696 A1 * | 10/2015 | Yamakawa | A61B 6/14 378/19 |

FOREIGN PATENT DOCUMENTS

| | | | |
|---|---|---|---|
| JP | 4571294 B2 | 10/2010 | |
| JP | 2011-245290 A | 12/2011 | |
| JP | 5184784 B2 | 4/2013 | |
| KR | 10-2005-0013417 A | 2/2005 | |
| WO | 2004/001567 A2 | 12/2003 | |
| WO | 2010025338 A1 | 3/2010 | |
| WO | WO-2012008492 A1 * | 1/2012 | ............ A61B 6/466 |

OTHER PUBLICATIONS

Communication dated Aug. 19, 2014, issued by the Korean Intellectual Property Office in counterpart Korean Application No. 10-2013-0032576.

Communication, dated Feb. 21, 2014, issued by the European Patent Office in counterpart European Application No. 13194357.3.

Communication dated Nov. 15, 2018 issued by the European Intellectual Property Office in counterpart European Application No. 13 194 357.3.

\* cited by examiner

| PLAN VIEW | REAR VIEW | OPERATION | FUNCTION |
|---|---|---|---|
|  |  | PUSH FORWARD | TABLE IN |
|  |  | PUSH FORWARD TO THE END | TABLE SCAN POSITION |
|  |  | PULL BACKWARD | TABLE OUT |
|  |  | PULL BACKWARD TO THE END | TABLE HOME |
|  |  | PRESS DOWN | LATERAL SETTING |

CONTROL APPARATUS OPERATIVELY COUPLED WITH MEDICAL IMAGING APPARATUS AND MEDICAL IMAGING APPARATUS HAVING THE SAME

CROSS-REFERENCE TO RELATED APPLICATIONS

This application is a continuation of U.S. patent application Ser. No. 14/095,133, filed on Dec. 3, 2013, in the U.S. Patent and Trademark Office, which claims priority from U.S. Provisional Patent Application No. 61/732,633, filed on Dec. 3, 2012, and Korean Patent Application No. 10-2013-0032576, filed on Mar. 27, 2013, in the Korean Intellectual Property Office, the disclosures of which are incorporated herein by reference in their entireties.

BACKGROUND

1. Field

Apparatuses and methods consistent with exemplary embodiments relate to a control apparatus which is operatively coupled with a medical imaging apparatus, which images an object, to remotely control the medical imaging apparatus, and a medical imaging apparatus having the same.

2. Description of the Related Art

In general, a medical imaging apparatus images the internal area of an object for diagnosing the object. For some medical imaging apparatuses, for example, a computed tomography (CT) apparatus and a magnetic resonance imaging (MRI) apparatus, a scan room to perform scanning of the object and a control room to control the scanning of the object are separated from each other.

The user, i.e., a radiologist, a technician, a medical professional, etc., controls a scan operation in the scan room by using a workstation or a host device located in the control room. The user may check the state of a patient through a shield glass installed between the control room and the scan room.

Devices for scan control are placed in front of the shield glass to enable the user to control the scan operation while checking the state of the patient over the shield glass. These devices may obstruct the user's view, making it difficult for the user to efficiently monitor the state of the patient.

SUMMARY

Exemplary embodiments may address at least the above problems and/or disadvantages and other disadvantages not described above. The exemplary embodiments are not required to overcome the disadvantages described above, and an exemplary embodiment may not overcome any of the problems described above.

One or more of exemplary embodiments provide a control apparatus which displays an image indicative of the state of a patient on a mobile display device and inputs a control command for a certain operation associated with a medical imaging apparatus through an input device docked with the mobile display device, so that the user may monitor the state of the patient in real time and perform a proper control operation based on the monitoring, and a medical imaging apparatus having the same.

In accordance with an aspect of an exemplary embodiment, a medical imaging apparatus, which images an internal area of an object, includes a scanner to scan the object to image the internal area of the object, a patient table to convey the object to the scanner, an imager mounted on at least one surface of the scanner, the imager capturing an image of the object on the patient table, and a mobile display device to display the image of the object captured by the imager.

The medical imaging apparatus may further include an input device docked with the mobile display device by wire or wirelessly.

The medical imaging apparatus may further include a controller to control the patient table, the controller being operatively coupled with the mobile display device.

When a control command signal for a movement of the patient table is transferred from the input device, the mobile display device may transmit the transferred control command signal to the controller.

The controller may control the patient table such that the patient table is moved in response to the control command signal.

The input device may include a jog shuttle moved forward or backward by an external force and then returning to an original position thereof.

The jog shuttle may input a control command for the movement of the patient table, and the controller may control the patient table such that a movement direction of the patient table is the same as a movement direction of the jog shuttle.

When the jog shuttle is moved forward to the end, the controller may control the patient table such that the patient table is moved to a preset scan position at once.

When the jog shuttle is moved backward to the end, the controller may control the patient table such that the patient table is moved to a preset home position at once.

When the jog shuttle is pressed down, the controller may control the patient table such that the patient table is laterally set to align a center of the object with a center of the scanner.

The controller may set and store the scan position by scan regions of the object.

The input device may include a touch panel.

When a drag signal from one point of a predefined area of the touch panel to another point of the predefined area is input, the controller may control the patient table such that the patient table is moved in a direction corresponding to a direction from the one point to the another point.

The controller may control the patient table such that the patient table is moved by an amount corresponding to a distance between the one point and the another point.

The touch panel may include at least one input unit to input a control command, the input unit being settable and changeable by a user.

The imager may include a wide-angle camera or a face-tracking camera.

The mobile display device may include a touch screen to recognize a touch signal, and a mobile controller to control the touch screen or the imager.

When a user selection for a region of interest (ROI) is input through the touch screen, the mobile controller may control the imager to zoom in the ROI.

When a drag signal corresponding to a predefined shape is input through the touch screen, the mobile controller may control the imager to zoom in on a center of an area corresponding to the drag signal by a preset magnification.

When a touch signal on one point is input through the touch screen, the mobile controller may control the imager to zoom in centering on the one point by a preset magnification.

The mobile controller may control the touch screen to display a language selection menu for provision of a breathing guide to the object, and provide the breathing guide in a language selected through the touch screen.

The mobile controller may recognize a motion of the object from the image of the object captured by the imager.

The mobile controller may output a warning visually or audibly upon recognizing the motion of the object.

The mobile controller may control the touch screen to display a blind control menu for control of blinds between a scan room in which the scanner is located and a control room in which the mobile display device is located, and control the blinds in response to a control command for the blinds input through the touch screen or the input device docked with the mobile display device.

The controller may control a scan operation of the scanner.

The input device may include a scan start key to input a command for start of the scan operation of the scanner, and a scan stop key to input a command for stop of the scan operation of the scanner.

The mobile display device may transmit a control command signal corresponding to the start of the scan operation to the controller when the command for the start of the scan operation is input from the input device.

The mobile display device may transmit a control command signal corresponding to the stop of the scan operation to the controller when the command for the stop of the scan operation is input from the input device.

In accordance with an aspect of an exemplary embodiment, a control apparatus, which is operatively coupled with a medical imaging apparatus which includes a patient table to convey an object, and an imager to capture an image of the object, includes a mobile display device to display the image of the object captured by the imager, and an input device docked with the mobile display device by wire or wirelessly.

The mobile display device may output a control command signal for a movement of the patient table transferred from the input device to the medical imaging apparatus.

The mobile display device may convert a format of the control command signal into a format transmittable to the medical imaging apparatus and output the format-converted signal to the medical imaging apparatus.

The input device may include a jog shuttle moved forward or backward by an external force and then returning to an original position thereof.

The jog shuttle may input a control command for the movement of the patient table, and the mobile display device may output the control command signal to move the patient table based on a movement direction of the jog shuttle.

The input device may include a touch panel.

When a drag signal from one point of a predefined area of the touch panel to another point of the predefined area is input, the mobile display device may output the control command signal to move the patient table in a direction corresponding to a direction from the one point to the another point.

The touch panel may include at least one input unit to input a control command, the input unit being settable and changeable by a user.

The mobile display device may include a touch screen to recognize a touch signal, and a mobile controller to control the touch screen.

When a user selection for a region of interest (ROI) is input through the touch screen, the mobile controller may control the imager to zoom in the ROI.

When a drag signal corresponding to a predefined shape is input through the touch screen, the mobile controller may control the imager to zoom in on a center of an area corresponding to the drag signal by a preset magnification.

When a touch signal on one point is input through the touch screen, the mobile controller may control the imager to zoom in centering on the one point by a preset magnification.

The mobile controller may control the touch screen to display a language selection menu for provision of a breathing guide to the object, and provide the breathing guide in a language selected through the touch screen.

The mobile controller may recognize a motion of the object from the image of the object captured by the imager.

The mobile controller may output a warning visually or audibly upon recognizing the motion of the object.

The mobile controller may control the touch screen to display a blind control menu for control of blinds between a scan room in which a scanner is located and a control room in which the mobile display device is located, and control the blinds in response to a control command for the blinds input through the touch screen or the input device docked with the mobile display device.

BRIEF DESCRIPTION OF THE DRAWINGS

The above and/or other aspects will become more apparent by describing in detail certain exemplary embodiments with reference to the accompanying drawings, in which.

DETAILED DESCRIPTION

Figure 1A:
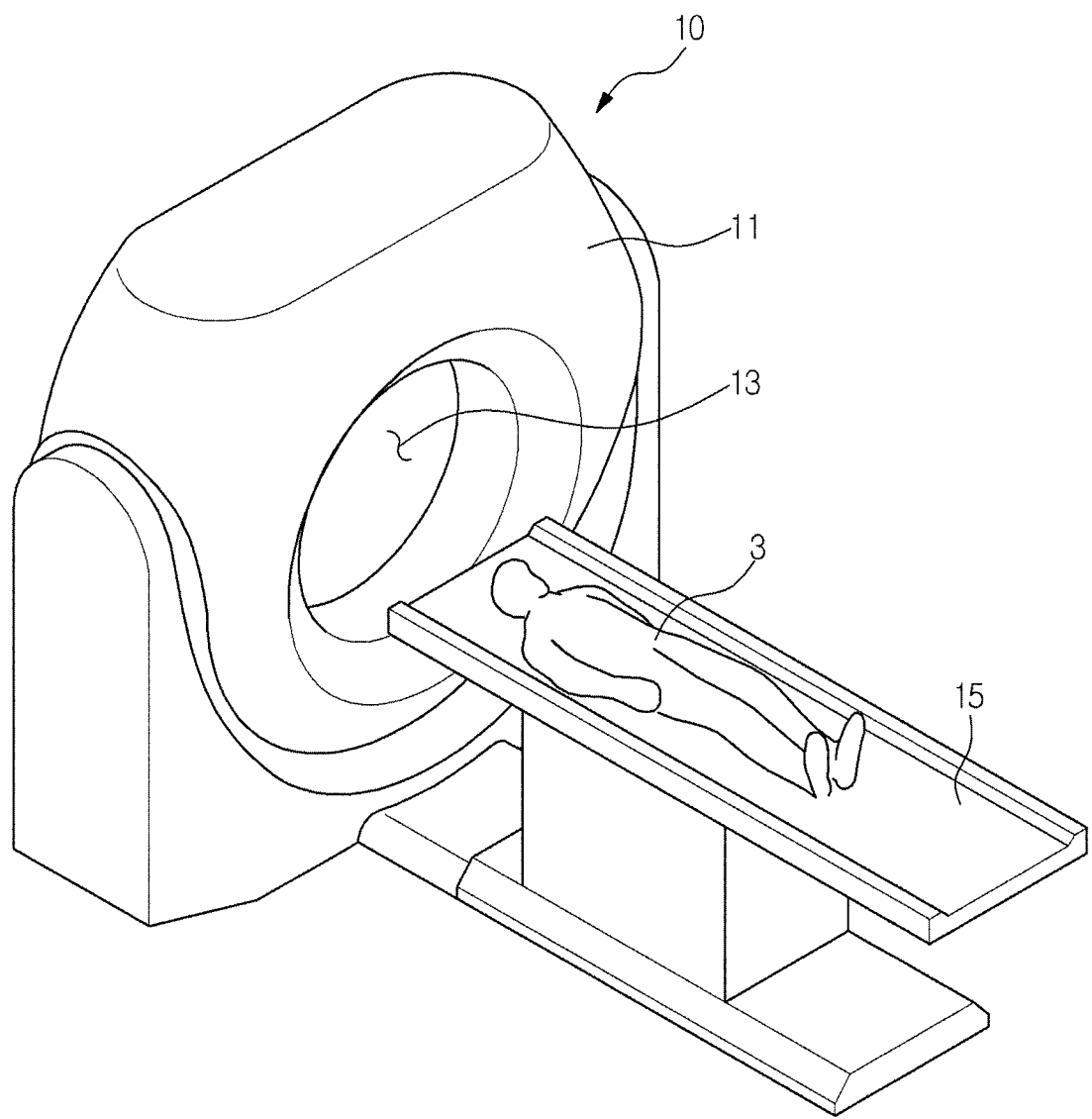
FIG. 1A is a perspective view showing the outer appearance of a computed tomography apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Figure 1B:
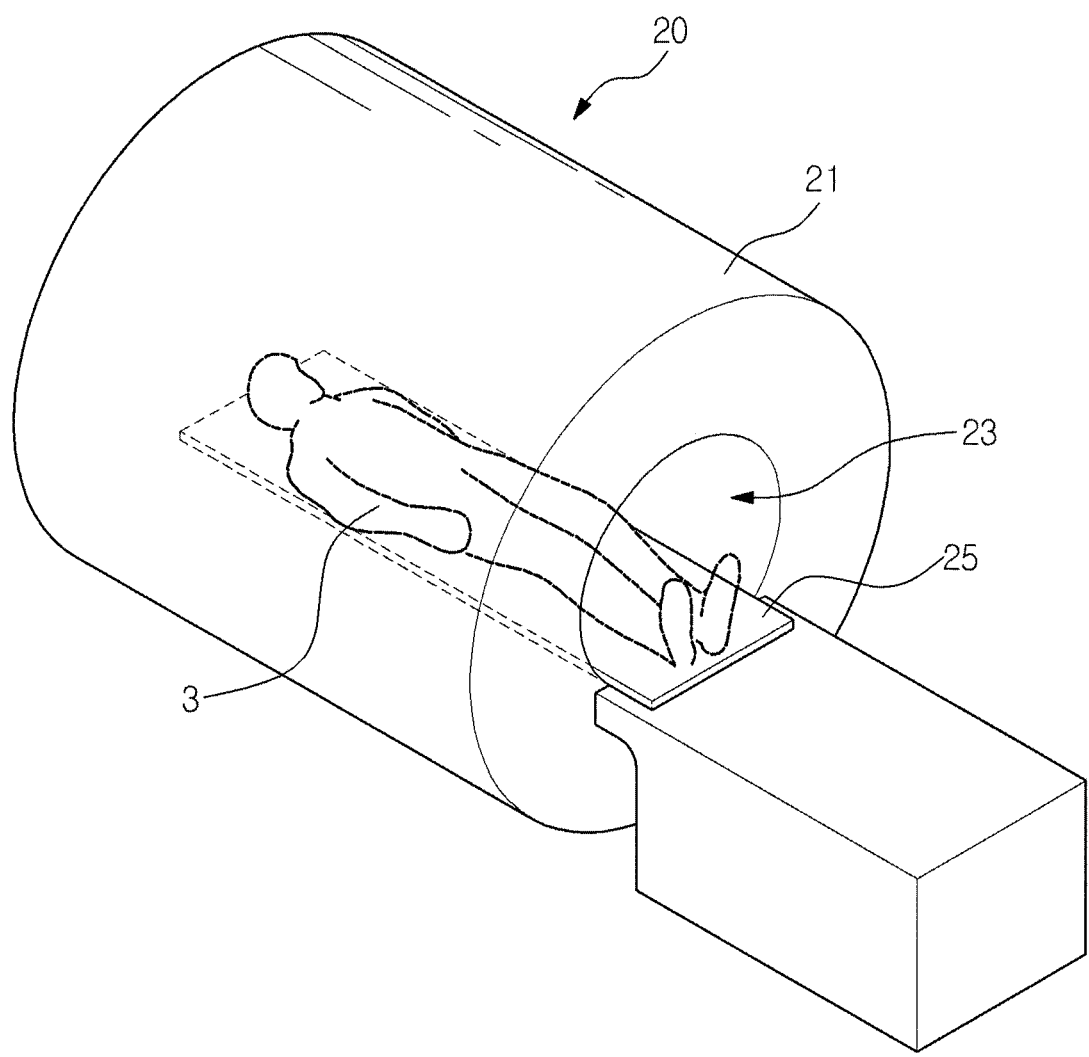
FIG. 1B is a perspective view showing the outer appearance of a magnetic resonance imaging apparatus.

FIG. 1A is a perspective view of a computed tomography (CT) apparatus, and FIG. 1B is a perspective view of a magnetic resonance imaging (MRI) apparatus.

Referring to FIG. 1A, the CT apparatus 10 has a gantry 11 to scan an object 3, which has a bore 13 formed at the center thereof. In the gantry 11, an X-ray source which generates and emits X-rays and an X-ray detector which detects X-rays transmitted through the object 3 are mounted to face each other. The object 3 is conveyed into the bore 13 while lying on a patient table 15. When a scan region of the object 3 is located at a scan position, the X-ray source and X-ray detector in the gantry 11 are rotated to emit and detect X-rays so as to scan the object 3.

Referring to FIG. 1B, the MRI apparatus 20 has a gantry 21 to scan the object 3, which has a bore 23 formed at the center thereof. In the gantry 21, a magnet assembly which forms a magnetic field within the bore 23 is mounted. When the object 3 is conveyed into the bore 23 while lying on a patient table 25, the magnet assembly mounted in the gantry 21 forms the magnetic field within the bore 23 to scan the object 3.

Figure 2:
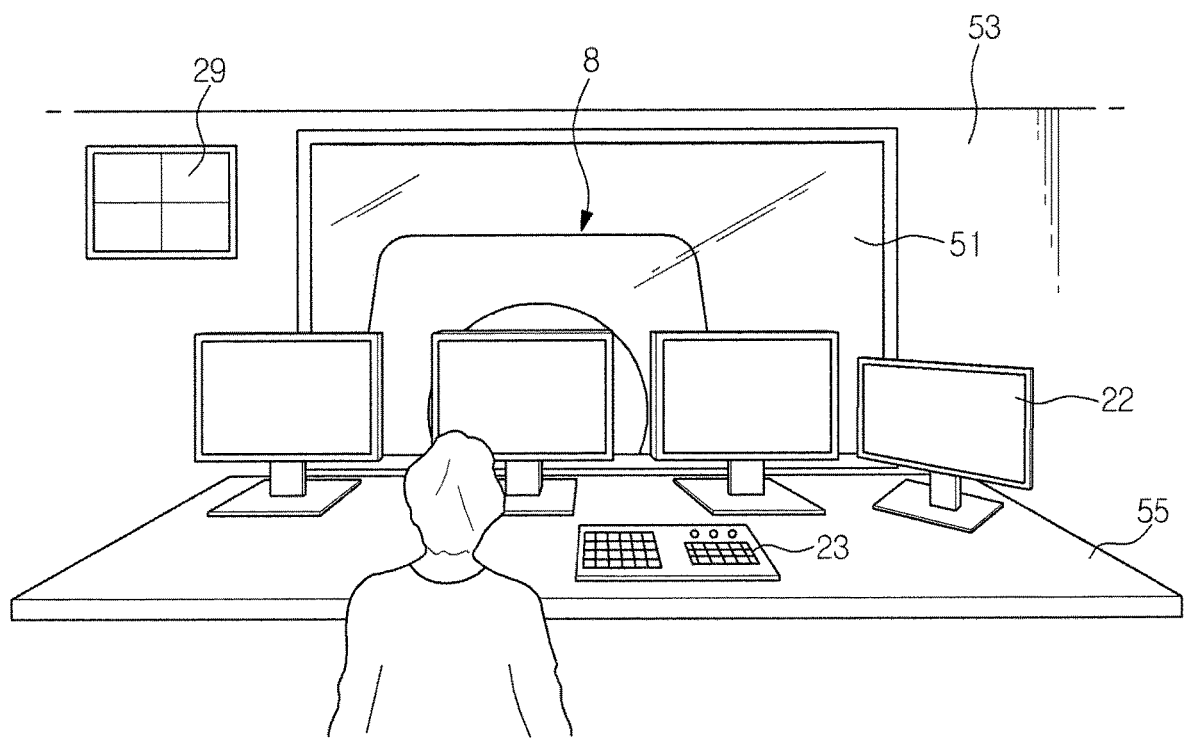
FIG. 2 is a view showing a work space of the user.

FIG. 2 shows a work space of the user.

A medical imaging apparatus, such as the CT apparatus 10 of FIG. 1A or the MRI apparatus 20 of FIG. 1B, has a gantry 8 located in a scan room as shown in FIG. 2. The scan room in which scanning of an object is performed and a control room in which control of the user is performed are separated from each other via a shield wall 53 having a shield glass 51.

In the control room, a host device which controls the medical imaging apparatus is located. The host device may be called a console or workstation. In an exemplary embodiment described below, a device which controls the operation of the medical imaging apparatus will be referred to as the host device for convenience of description.

The host device includes one or more display devices 22 to display a scan image of the object, and one or more input devices 23 to input a control command from the user. Generally, in order to enable the user to control the medical imaging apparatus while checking the state of the object through the shield glass 51, a work table 55 is placed in front of the shield glass 51 and a plurality of display devices 22 and a plurality of input devices 23 are placed on the work table 55. However, in this arrangement, the display devices 22 may obstruct the user's view, thereby causing the user to fail to smoothly check the state of the object, resulting in difficulty in properly controlling the medical imaging apparatus based on the state of the object.

In order to enable the user to check the state of the object, an image of the inside of the scan room may be captured through a closed-circuit television (CCTV) and then displayed through a display device 29 mounted on the shield wall 53 at the side of the control room. However, the display device 29 mounted on the shield wall 53 is out of sight of the user who controls the medical imaging apparatus in front of the work table 55, resulting in difficulty in monitoring the object in real time.

Figure 3:
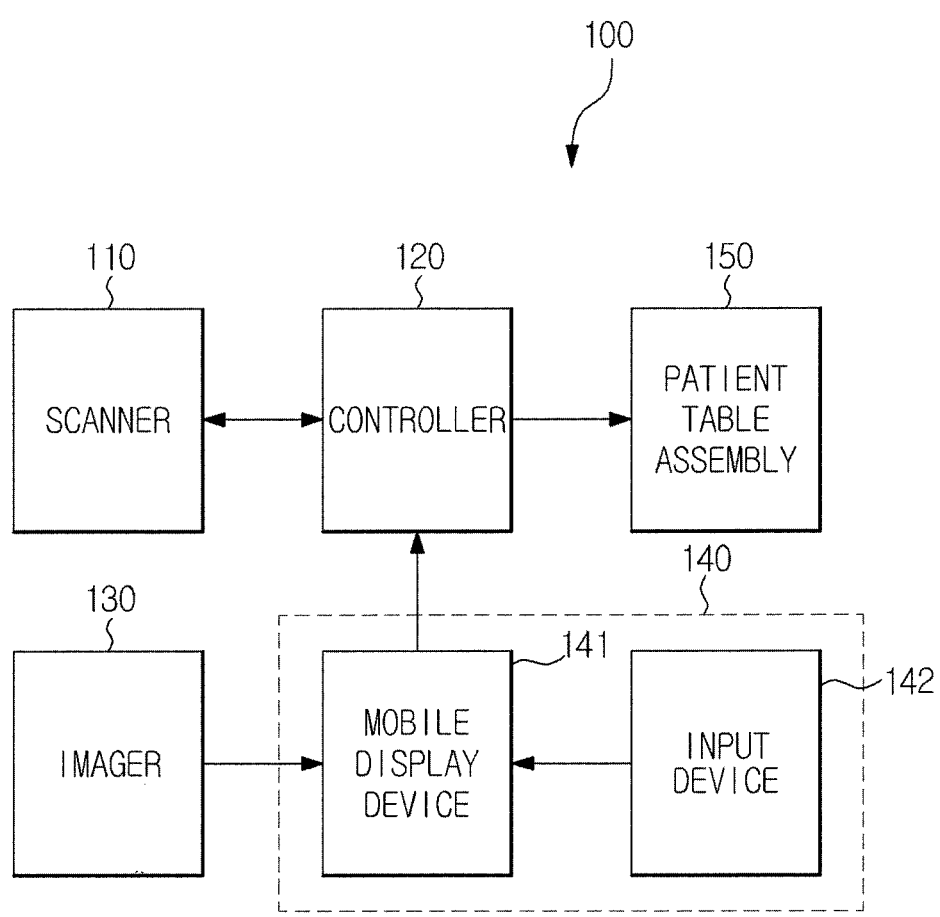
FIG. 3 is a block diagram of a control apparatus and a medical imaging apparatus having the same according to an exemplary embodiment.

FIG. 3 is a block diagram of a control apparatus and a medical imaging apparatus having the same according to an exemplary embodiment.

Referring to FIG. 3, the medical imaging apparatus 100, according to an exemplary embodiment, includes a scanner 110 to scan an object, a controller 120 to control the overall operation of the medical imaging apparatus 100, a patient table assembly 150 to convey the object to a scan position, an imager 130 to capture an image of the object on a patient table, and the control apparatus 140. The control apparatus 140 functions to display the captured image of the object and remotely control a movement of the patient table or a scan operation of the scanner 110. The control apparatus 140 includes a mobile display device 141, and an input device 142 coupled with the mobile display device 141.

In an exemplary embodiment, the scanner 110 may include a CT apparatus or an MRI apparatus. The controller 120 may have all or some of functions performed by a host device of the CT apparatus or MRI apparatus.

Although the mobile display device 141 is shown in the block diagram of FIG. 3 as controlling the scanner 110 and the patient table assembly 150 through the controller 120, it may directly control the scanner 110 and the patient table assembly 150. In this case, the mobile display device 141 may generate a control signal for the scanner 110 or patient table assembly 150 in response to a control command signal transferred from the input device 142 and may directly transmit the generated control signal to the scanner 110 or patient table assembly 150. However, for convenience of description, the following description will be given on the assumption that the mobile display device 141 controls the scanner 110 and the patient table assembly 150 through the controller 120.

The medical imaging apparatus 100 according to an exemplary embodiment is not limited in type and the control apparatus 140 according to an exemplary embodiment is applicable to the medical imaging apparatus 100 irrespective of the type thereof. In this regard, any medical imaging apparatus is applicable to an exemplary embodiment so long as it uses remote control. However, for convenience of description, the following description is provided for a CT apparatus or an MRI apparatus, according to an exemplary embodiment.

Figure 4:
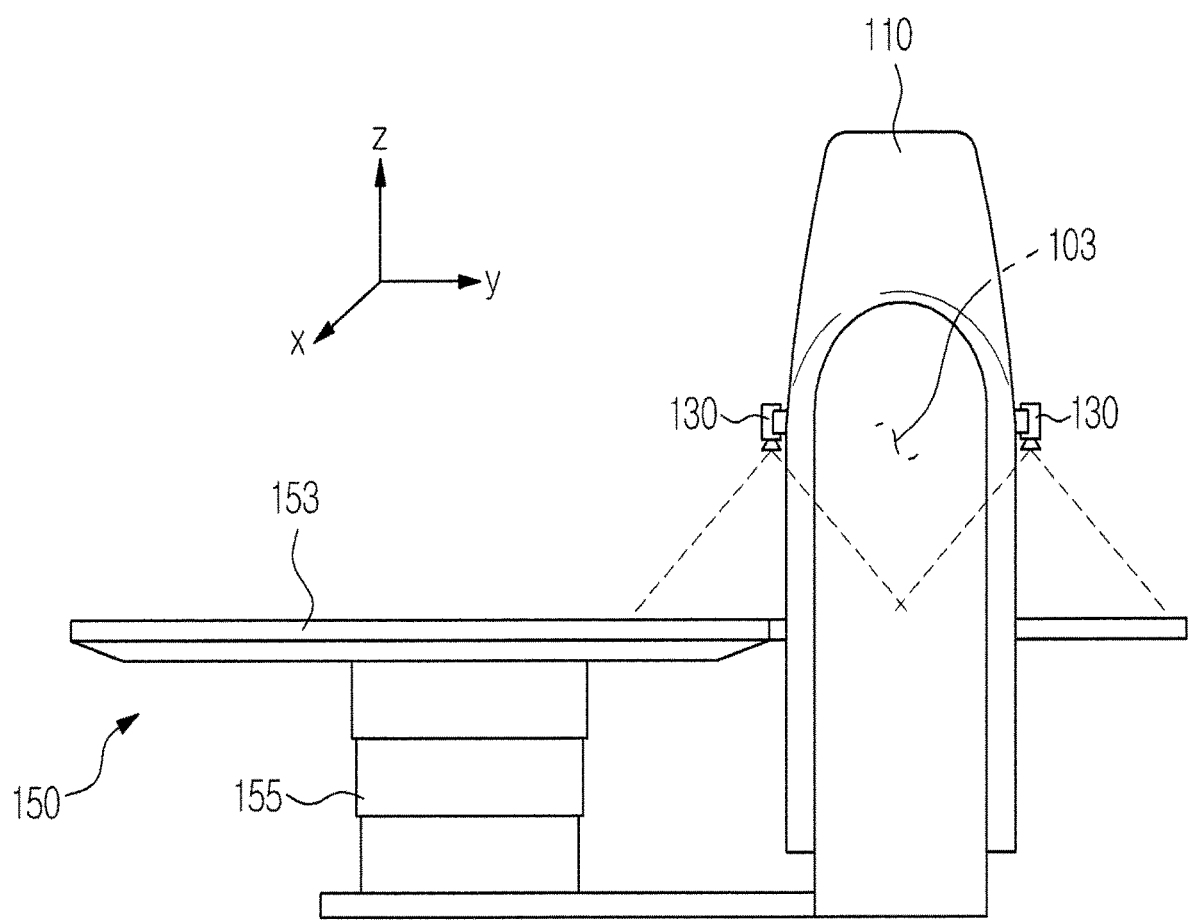
FIG. 4 is a view showing the outer appearance of a scanner equipped with an imager.

FIG. 4 shows the scanner equipped with the imager.

Referring to FIG. 4, the imager 130, which captures an image of the object, may be mounted on the front surface or rear surface of the scanner 110. The imager 130 may be mounted on one of the front surface and rear surface of the scanner 110, or on both the front surface and rear surface of the scanner 110 as shown in FIG. 4.

The imager 130 may include a wide-angle camera or face-tracking camera. In order to enable the user to check the current state of the object to cope with an emergency or control the scan operation, the face of the object needs to be captured. In this regard, provided that the imager 130 includes a face-tracking camera, the face of the object may appear on an image of the object captured during scanning even if the scan region is not the upper part of the object.

Alternatively, sometimes, the scan region of the object may need to be checked together with the face of the object. In this case, provided that the imager 130 includes a wide-angle camera having a shooting range capable of covering the whole of the object, the face of the object may appear on an image of the object even if the object is being conveyed by the patient table 153 which is supported by a support 155, or the scan region is not the upper part of the object.

An image of the object captured by the imager 130 is displayed on the mobile display device 141. Therefore, the user may set the mobile display device 141 at a desired position to control the movement of the patient table 153 and the scan operation while monitoring the state of the object.

Figure 5A:
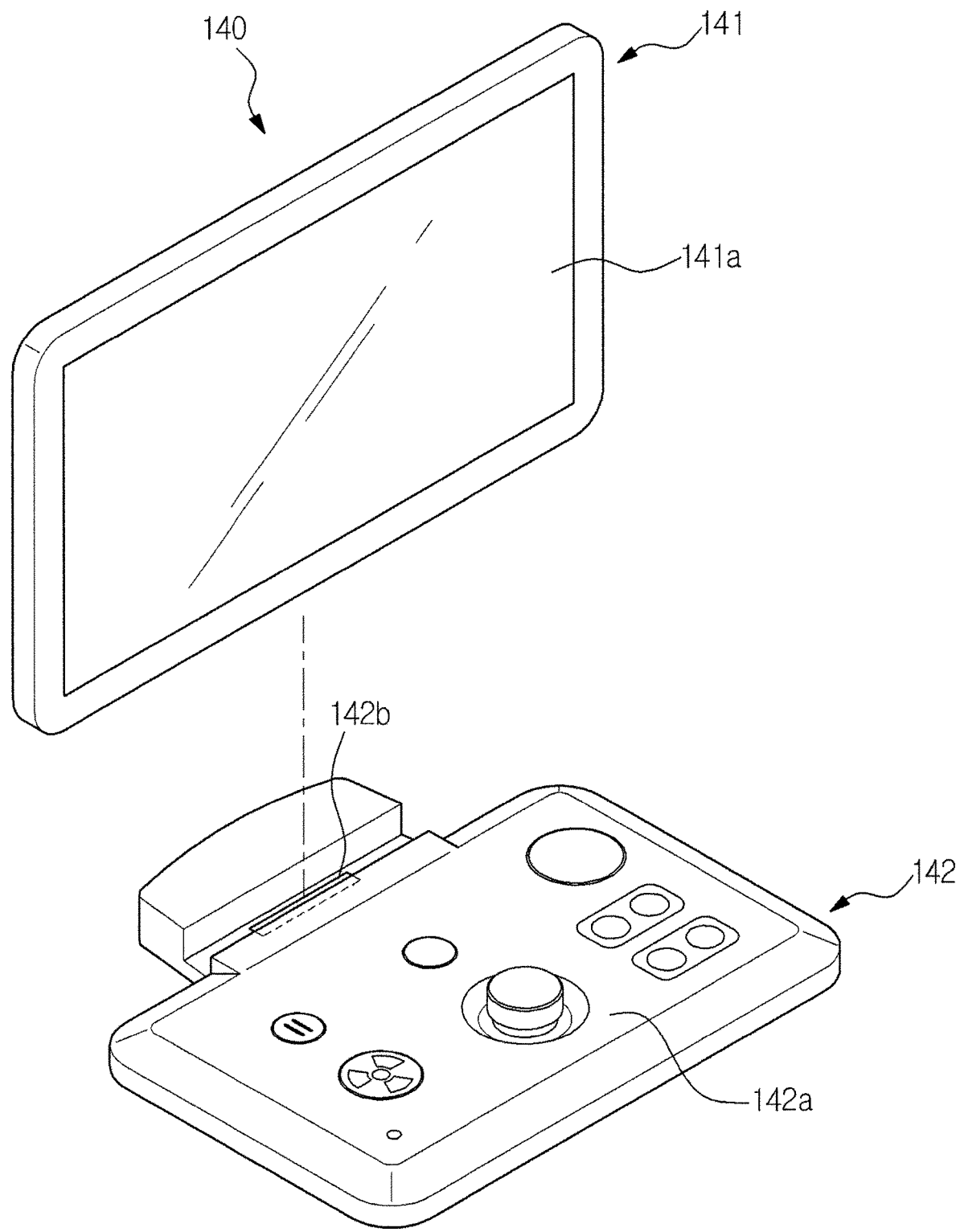
FIGS. 5A and 5B are views showing the outer appearance of the control apparatus according to an exemplary embodiment.
Figure 5B:
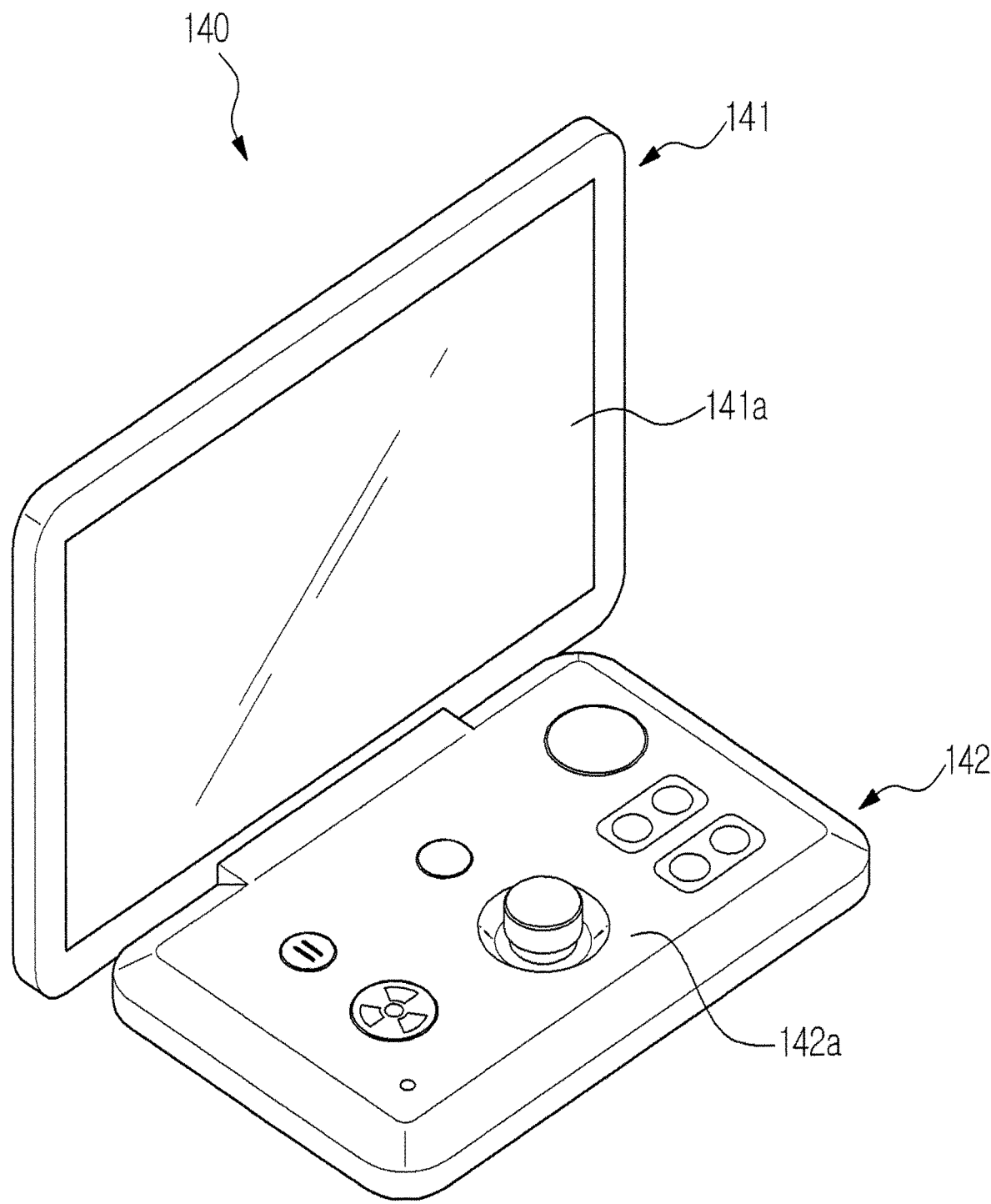

FIGS. 5A and 5B show the control apparatus according to an exemplary embodiment.

Referring to FIG. 5A, the mobile display device 141 includes a display 141a to display an image, and may be a portable device. For example, the mobile display device 141 may include a touch pad, a tablet personal computer (PC), a smart phone, a personal digital assistant (PDA), or the like, and the display 141a may include a screen employing a liquid crystal display (LCD), a light emitting diode (LED) or an organic LED (OLED), or a touch screen.

The input device 142 includes an input unit 142a to input various control commands from the user. The input unit 142a may include buttons as shown in FIG. 5A, and/or a touch panel. The configuration of the input unit 142a will be described later in detail.

Referring to FIG. 5B, the input device 142 may be docked with the mobile display device 141 to transfer a control command input through the input unit 142a to the mobile display device 141. In addition, the mobile display device 141 may be charged through the docking. Although the input device 142 and the mobile display device 141 may be docked through a terminal 142b for docking (shown in FIG. 5A), an exemplary embodiment is not limited thereto. For example, the input device 142 and the mobile display device 141 may be docked just when the mobile display device 141 is placed on the input device 142 or attached to the input device 142, or when the mobile display device 141 and the input device 142 are separated from each other.

The mobile display device 141 and the input device 142 are freely detachably mounted to each other. As needed, the user may dock the mobile display device 141 with the input device 142 to use the mobile display device 141 together with the input device 142, or separate the mobile display device 141 from the input device 142 to use the mobile display device 141 separately from the input device 142.

Figure 6:
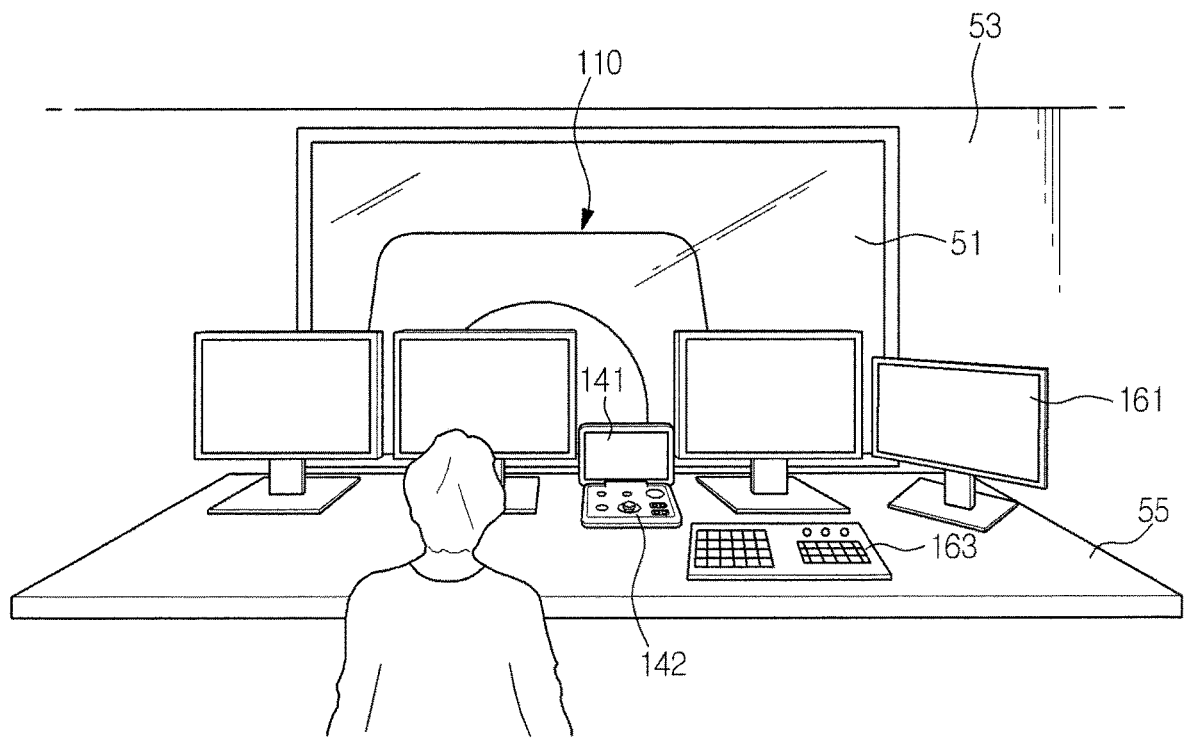
FIG. 6 is a view showing a work space of the user in the medical imaging apparatus according to an exemplary embodiment.

FIG. 6 shows a work space of the user in the medical imaging apparatus according to an exemplary embodiment.

The user may set the mobile display device 141 and the input device 142 at a desired position for use. As shown in FIG. 6, a work table 55 of the user is placed in front of a shield glass 51 which separates a scan room and a control room from each other, and one or more main input devices 163 and one or more main display devices 161 are arranged on the work table 55 to control the overall operation of the medical imaging apparatus or display a scan image. A plurality of main display devices 161 and a plurality of main input devices 163 may be arranged on the work table 55.

The arrangement of the plurality of main display devices 161 in front of the shield glass 51 may obstruct the user's view, thereby making it difficult for the user to check the state of the object directly through the shield glass 51. Provided that the mobile display device 141 which displays an image of the object captured by the imager 130 and the input device 142 which is docked with the mobile display device 141 are arranged on the work table 55 in front of the shield glass 51 as shown in FIG. 6, the user may, at the work table 55, check the state of the object through the mobile display device 141 and control the movement of the patient table 153 or the scan operation through the input device 142. Further, the user may also perform a control operation using the main display device 161 or main input device 163 without shifting his/her position or moving his/her view far away.

Figure 7:
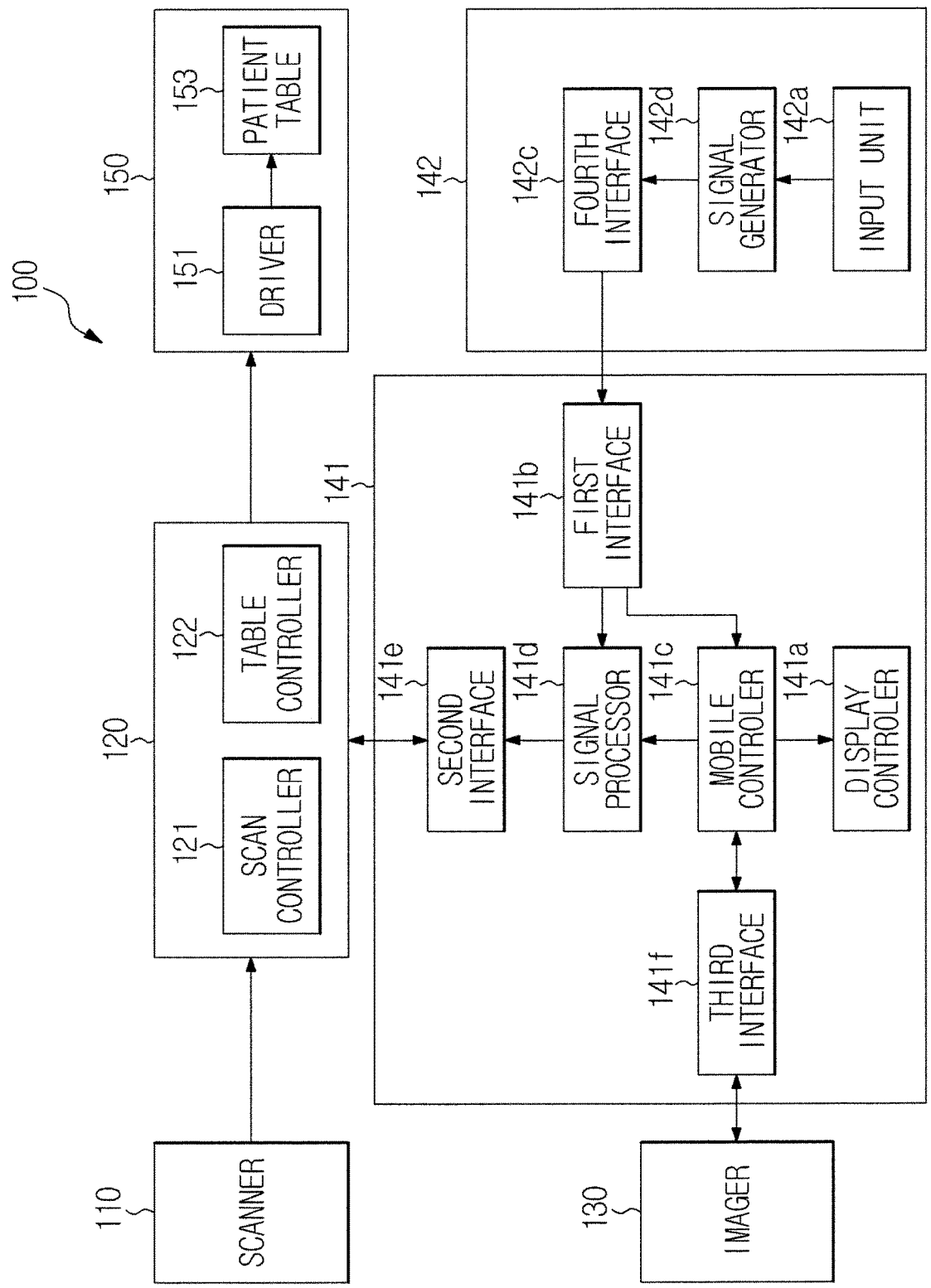
FIG. 7 is a detailed block diagram of the medical imaging apparatus according to an exemplary embodiment.

FIG. 7 is a detailed block diagram of the medical imaging apparatus according to an exemplary embodiment.

Referring to FIG. 7, the input device 142 includes the input unit 142a to input a control command from the user, a signal generator 142d to sense the input of the control command and generate a signal corresponding to the input control command (referred to hereinafter as a control command signal), and an fourth interface 142c to perform docking with the mobile display device 141.

The mobile display device 141 includes a first interface 141b to perform docking with the input device 142, a signal processor 141d to process a control command signal transferred from the input device 142 to convert the format of the control command signal into a format transmittable to other peripheral components including the controller 120, a second interface 141e to transmit the processed control command signal to the controller 120, a third interface 141f to receive an image signal of the object from the imager 130, a mobile controller 141c to process the image signal of the object and input the processed image signal to the display 141a, and the display 141a to display an image of the object based on the image signal input from the mobile controller 141c.

The controller 120 includes a scan controller 121 to control the scan operation of the scanner 110, and a table controller 122 to control the movement of the patient table 153. The patient table assembly 150 includes the patient table 153, and a driver 151 to drive the patient table 153. The driver 151 may include a motor to supply power to the patient table 153, and a driver controller to drive the motor.

Hereinafter, the operation of each component of the medical imaging apparatus 100 will be described in detail.

An image signal of the object acquired by the imager 130 is transmitted to the mobile display device 141 through the third interface 141f of the mobile display device 141. The third interface 141*f* may be implemented with a wireless network interface such as a wireless personal area network (WPAN), for example, Bluetooth or ZigBee, or a wireless local area network (WLAN). Alternatively, the image signal of the object acquired by the imager 130 may be transmitted to the mobile display device 141 through the second interface 141*e* via the controller 120.

The mobile controller 141*c* controls the display 141*a* to display an image on the display 141*a*. For example, the mobile controller 141*c* may process the image signal of the object acquired by the imager 130 and display an image based on the processed image signal through the display 141*a*. In detail, the mobile controller 141*c* may decode the image signal of the object transmitted in a compressed signal format, convert the format of the decoded image signal into a format appropriate to a display mode of the display 141*a*, and input the resulting image signal to the display 141*a*. The mobile controller 141*c* may also control the overall operation of the mobile display device 141 in addition to controlling the display 141*a*.

The mobile display device 141 may be docked with the input device 142 to share input/output signals with the input device 142. In an exemplary embodiment, interconnecting two or more physically separated devices is referred to as docking, which includes a wired mode and/or a wireless mode. The wireless mode includes docking based on physical coupling between two devices and docking in a separated state without physical coupling between two devices. For docking, each of the first interface 141*b* of the mobile display device 141 and the fourth interface 142*c* of the input device 142 may be implemented with a serial port, a parallel port, a universal serial bus (USB) port, an infrared port, or the like, or be implemented with a wireless network interface such as a WPAN, for example, Bluetooth or ZigBee.

When docking is made between the mobile display device 141 and the input device 142, a control command signal corresponding to a control command from the user is transferred to the mobile display device 141 through the fourth interface 142*c* of the input device 142 and the first interface 141*b* of the mobile display device 141.

The signal processor 141*d* converts the format of the transferred control command signal into a format transmittable to the controller 120, and the second interface 141*e* transmits the format-converted control command signal to the controller 120. The second interface 141*e* may be implemented with a wireless network interface such as a WPAN, for example, Bluetooth or ZigBee.

When the control command signal transmitted from the mobile display device 141 is associated with the scan operation of the scanner 110, the scan controller 121 controls the scanner 110 in response to the control command signal. When the control command signal transmitted from the mobile display device 141 is associated with the movement of the patient table 153, the table controller 122 controls the movement of the patient table 153 in response to the control command signal.

In detail, the user may input a control command associated with the movement of the patient table 153 by operating the input unit 142*a* while viewing an image of the object displayed on the display 141*a*. A control command signal corresponding to the control command associated with the movement of the patient table 153 is transmitted through the mobile display device 141 to the table controller 122, which then generates a control signal corresponding to the control command signal and transmits the generated control signal to the driver 151.

The driver controller of the driver 151 supplies current corresponding to the transmitted control signal to the motor such that the patient table 153 is moved in response to the control command from the user.

The user may input a control command associated with the scan operation of the scanner 110 by operating the input unit 142*a* while viewing an image of the object displayed on the display 141*a*. For example, in the case where the input unit 142*a* of the input device 142 has a function of inputting a command for the start or stop of the scan operation, the user may input the command for the start or stop of the scan operation by operating the input unit 142*a*. A control command signal corresponding to the input command is transferred to the mobile display device 141 and transmitted to the scan controller 121 through the second interface 141*e*. The scan controller 121 may start or stop the scan operation in response to the control command signal.

The scanner 110 is configured to scan the object. In the case where an image generated by the medical imaging apparatus 100 is a CT image, the scanner 110 includes an X-ray source to generate X-rays and emit the generated X-rays to the object, and an X-ray detector to detect X-rays transmitted through the object. The X-ray source and the X-ray detector may be implemented into one module so as to be rotated together when CT imaging is performed. The scanner 110 may further include a high voltage generator to supply a high voltage to the X-ray source. In the case where an image generated by the medical imaging apparatus 100 is a magnetic resonance image, the scanner 110 includes a magnet assembly to form a magnetic field. The magnet assembly includes a static field coil to form a static field, a gradient field coil to form a gradient field in the static field, and a radio frequency (RF) coil to apply an RF pulse to an atomic nucleus to excite the atomic nucleus, and receive an echo signal from the atomic nucleus.

When the control command signal corresponding to the start of the scan operation is transmitted from the mobile display device 141, the scan controller 121 supplies power to the scanner 110 such that the scanner 110 generates and detects X-rays or forms a magnetic field within a bore 103.

The control command signal output from the mobile display device 141 may be transmitted to the scanner 110 or patient table assembly 150.

Hereinafter, a more detailed description will be given of the operation of the medical imaging apparatus 100 in which the control apparatus 140 is operatively coupled with the other components.

Figure 8:
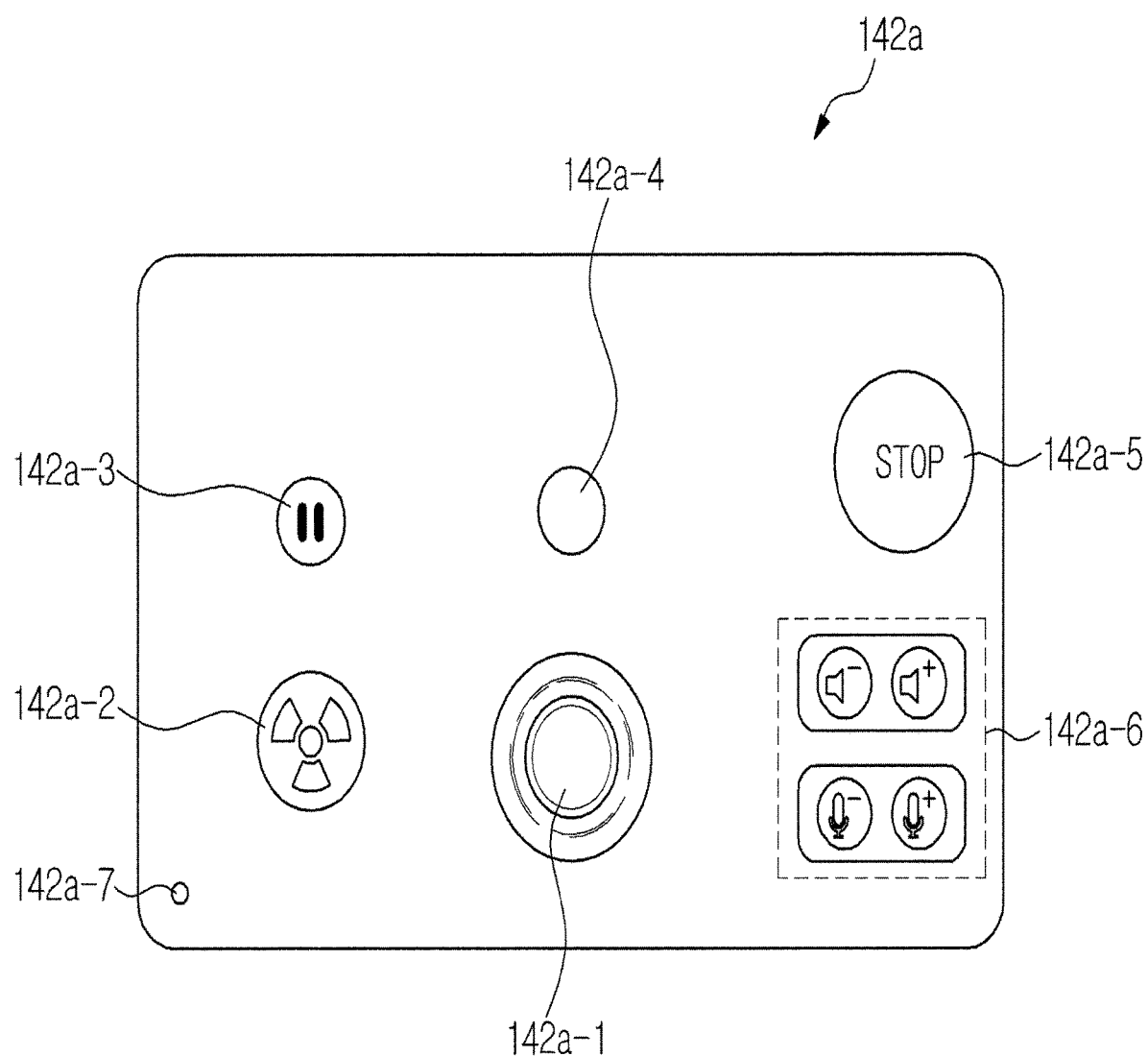
FIG. 8 is a view showing an example of the configuration of an input unit provided in an input device.

FIG. 8 shows an example of the configuration of the input unit 142*a* provided in the input device 142. FIG. 8 is a plan view of the input unit 142*a*. In an exemplary embodiment, the input unit 142*a* is implemented in a button manner. Here, the button manner signifies a manner in which the user can input a control command by applying an external force in a physical form such as pushing or pulling, and may include all input manners other than a touch manner. The following description will be given on the assumption that the input unit 142*a* includes a plurality of keys, each of which may be implemented in the button manner or the touch manner.

The input unit 142*a* may have various functions corresponding to controllable operations of the medical imaging apparatus 100. As an example, the input unit 142*a* may include a table movement key 142*a*-1 to input a command for the movement of the patient table, a scan start key 142*a*-2 to input a command for the start of the scan operation of the scanner 110, a scan pause key 142*a*-3 to temporarily stop the scan operation of the scanner 110, a laser marker key 142*a*-4 to turn on/off a laser marker indicative of the scan position of the scanner 110, an emergency stop key 142a-5 to stop the scan operation in an emergency, a sound level key 142a-6 to adjust a sound output level, and a microphone 142a-7 to input the user's voice.

The table movement key 142a-1 may be implemented as a jog shuttle. Hereinafter, an operation of controlling the patient table 153 using the jog shuttle will be described in detail.

Figure 9A:
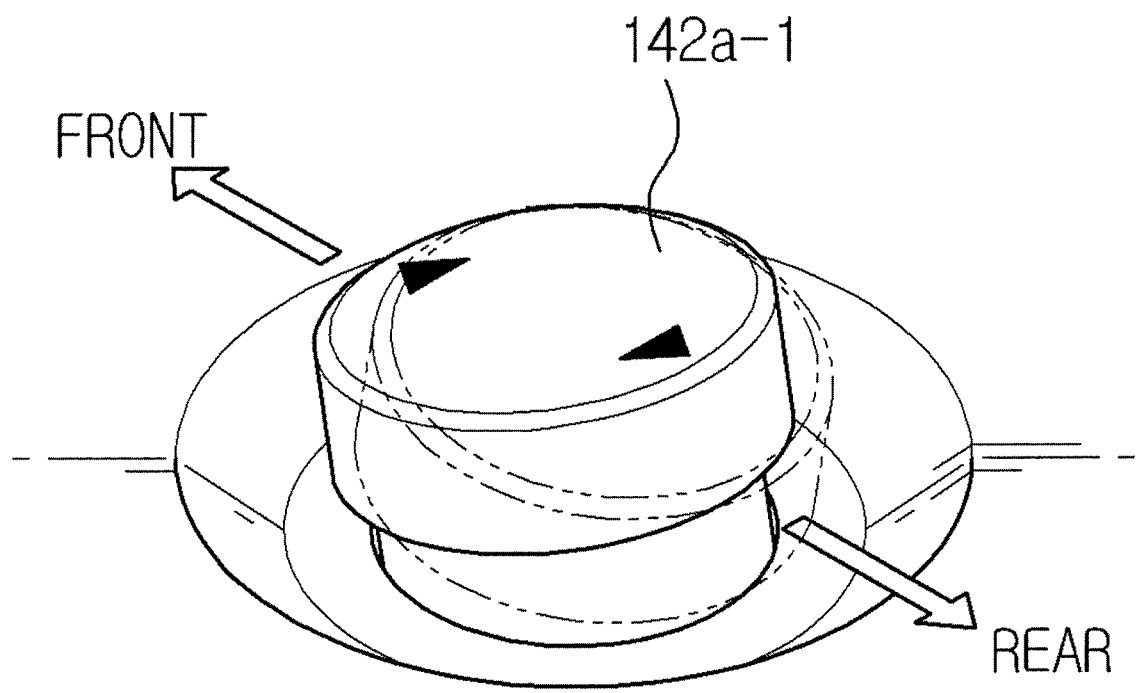
FIG. 9A is a perspective view illustrating operations of a jog shuttle.
Figure 9B:
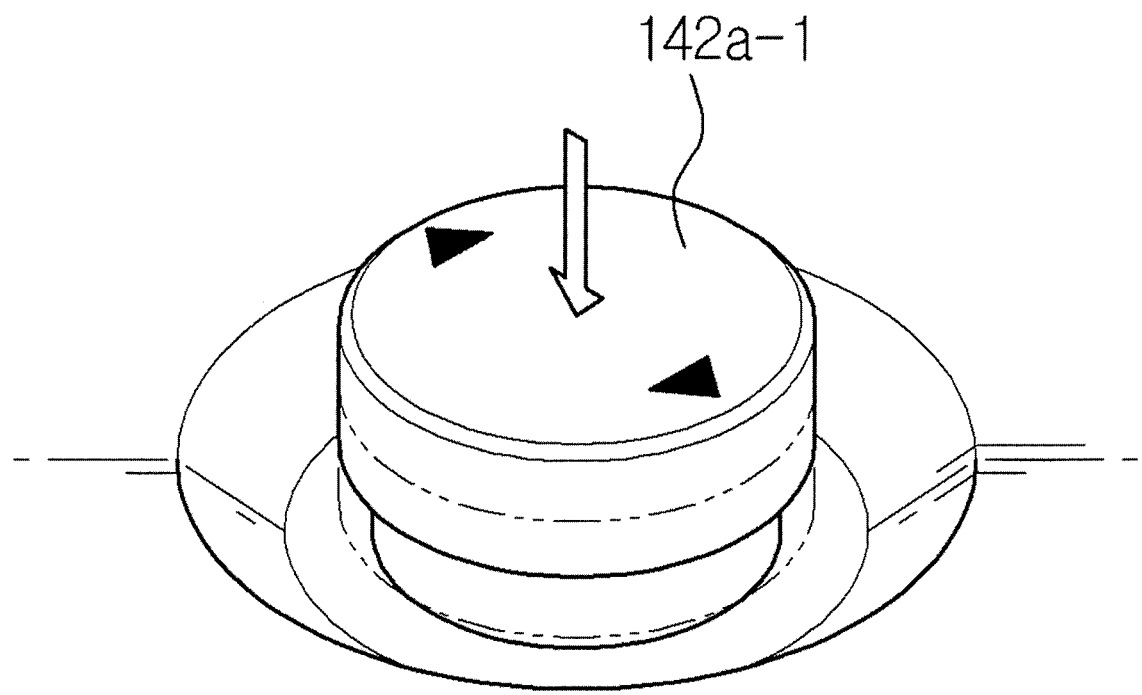
FIG. 9B is a perspective view illustrating operations of a jog shuttle.
Figure 9C:
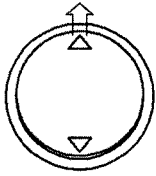
FIG. 9C is a table illustrating movements of a patient table based on the operations of the jog shuttle.
Figure 9C:
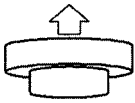
Figure 9C:
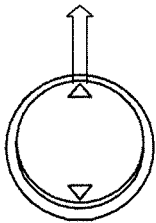
Figure 9C:
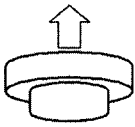
Figure 9C:
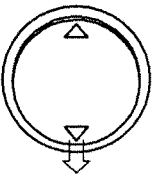
Figure 9C:
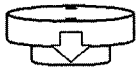
Figure 9C:
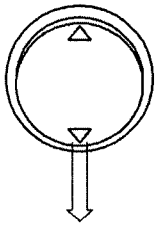
Figure 9C:
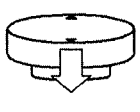
Figure 9C:
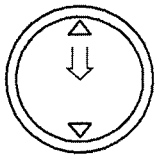
Figure 9C:
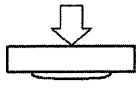

FIGS. 9A and 9B are perspective views illustrating operations of the jog shuttle, and FIG. 9C is a table illustrating movements of the patient table based on the operations of the jog shuttle.

Referring to FIG. 9A, the table movement key 142a-1 is the jog shuttle, so that it may be moved forward or backward by an external force and then return to its original position. The jog shuttle may input a signal by even a small amount of external force applied thereto. In this regard, provided that the table movement key 142a-1 is the jog shuttle, the user may input a control command by pushing or pulling the jog shuttle just lightly.

In addition, when the table movement key 142a-1 implemented as the jog shuttle is pressed down (shown in FIG. 9B), it may be moved downward and then return to its original position. In this regard, operations of the table movement key 142a-1 may be set to correspond to user control commands, respectively. Therefore, an operation of the table movement key 142a-1 may be recognized, and a corresponding control command signal may be generated and transmitted to the table controller 122.

As an example, as shown in FIG. 9C, when the table movement key 142a-1 is pushed forward, the patient table 153 may be moved into the bore 103 of the scanner 110. A distance at which the patient table 153 is moved when the table movement key 142a-1 is pushed once may be preset. The distance may be set as a default or set and changed by the user.

When the table movement key 142a-1 is pushed forward to the end, the patient table 153 may be moved to a preset scan position at once. The scan position may be different according to every scan region of the object. Therefore, scan positions may be preset with respect to respective scan regions, and, when a scan region of the object is input, the patient table 153 may be moved to a scan position corresponding to the input scan region.

When the table movement key 142a-1 is pulled backward, the patient table 153 may be moved out of the bore 103. If the table movement key 142a-1 is pushed from the forward side to the backward side, the operation of pulling the table movement key 142a-1 backward may be established. A distance at which the patient table 153 is moved when the table movement key 142a-1 is pulled once may also be preset. The distance may be set as a default or set and changed by the user.

When the table movement key 142a-1 is pulled backward to the end, the patient table 153 may be moved to a preset home position at once. The home position is a position at which the object can get off the patient table 153, and may be preset.

When the table movement key 142a-1 is pressed down, the patient table 153 may be laterally set. That is, the above-described movements of the patient table 153, in and out of the bore, are movements in a y-axis direction, and the lateral setting is to move the patient table 153 in an x-axis direction. In detail, the lateral setting is to move the patient table 153 in the x-axis direction such that the center of the object and the center of the bore 103 are aligned on an x-axis.

For example, the patient table 153 may be moved in a −x-axis direction when the center of the object leans in a +x-axis direction, and in the +x-axis direction when the center of the object leans in the −x-axis direction. The imager 130 may sense the position of the face of the object and transmit the sensing result to the table controller 122. When the table movement key 142a-1 is pressed down, a control command signal for the lateral setting is transmitted to the table controller 122, which then moves the patient table 153 in the x-axis direction based on the face position of the object transmitted from the imager 130 such that the center of the object is aligned with the center of the bore 103.

Figure 10A:
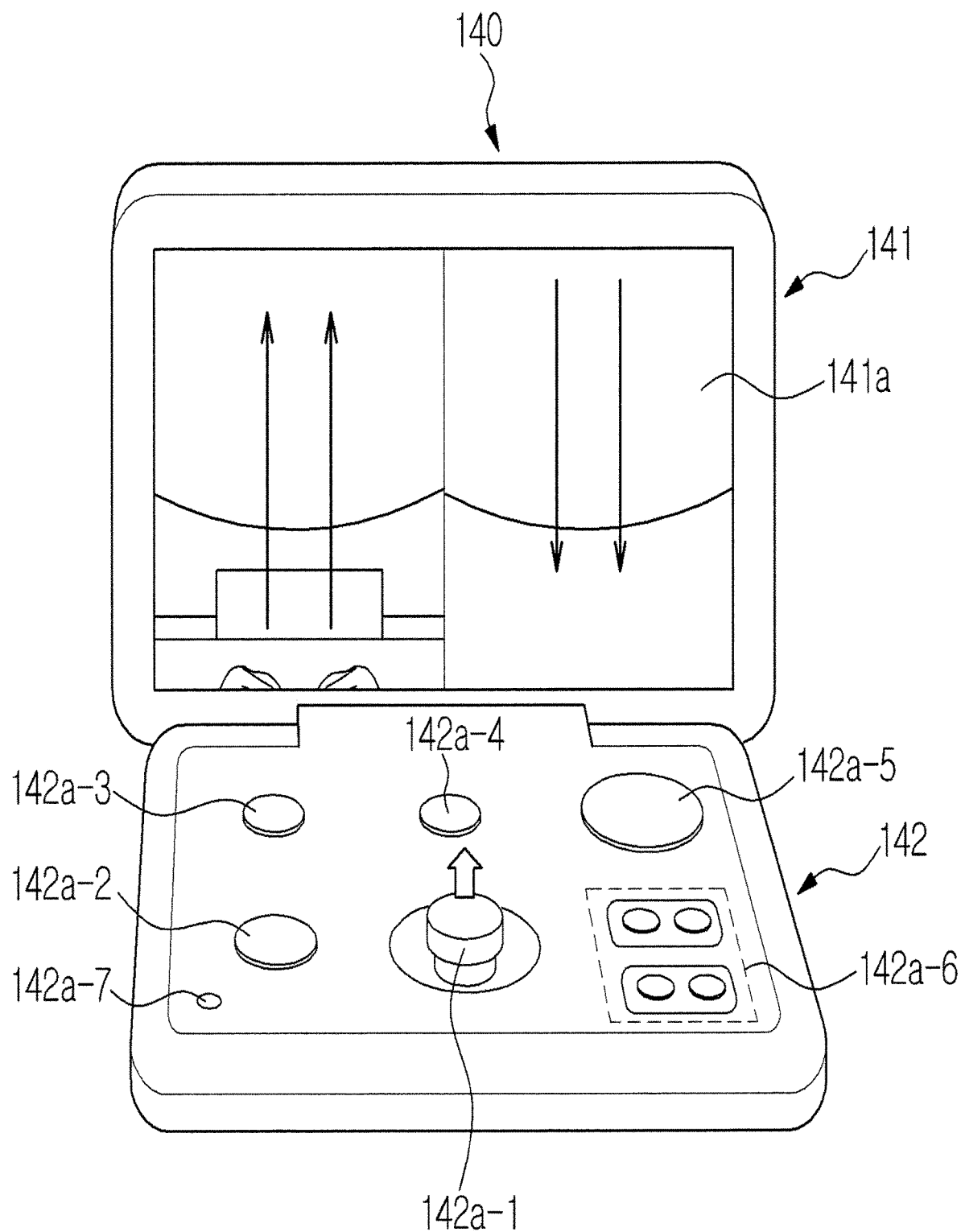
FIGS. 10A and 10B are views illustrating in detail an operation of moving the patient table using the control apparatus.
Figure 10B:
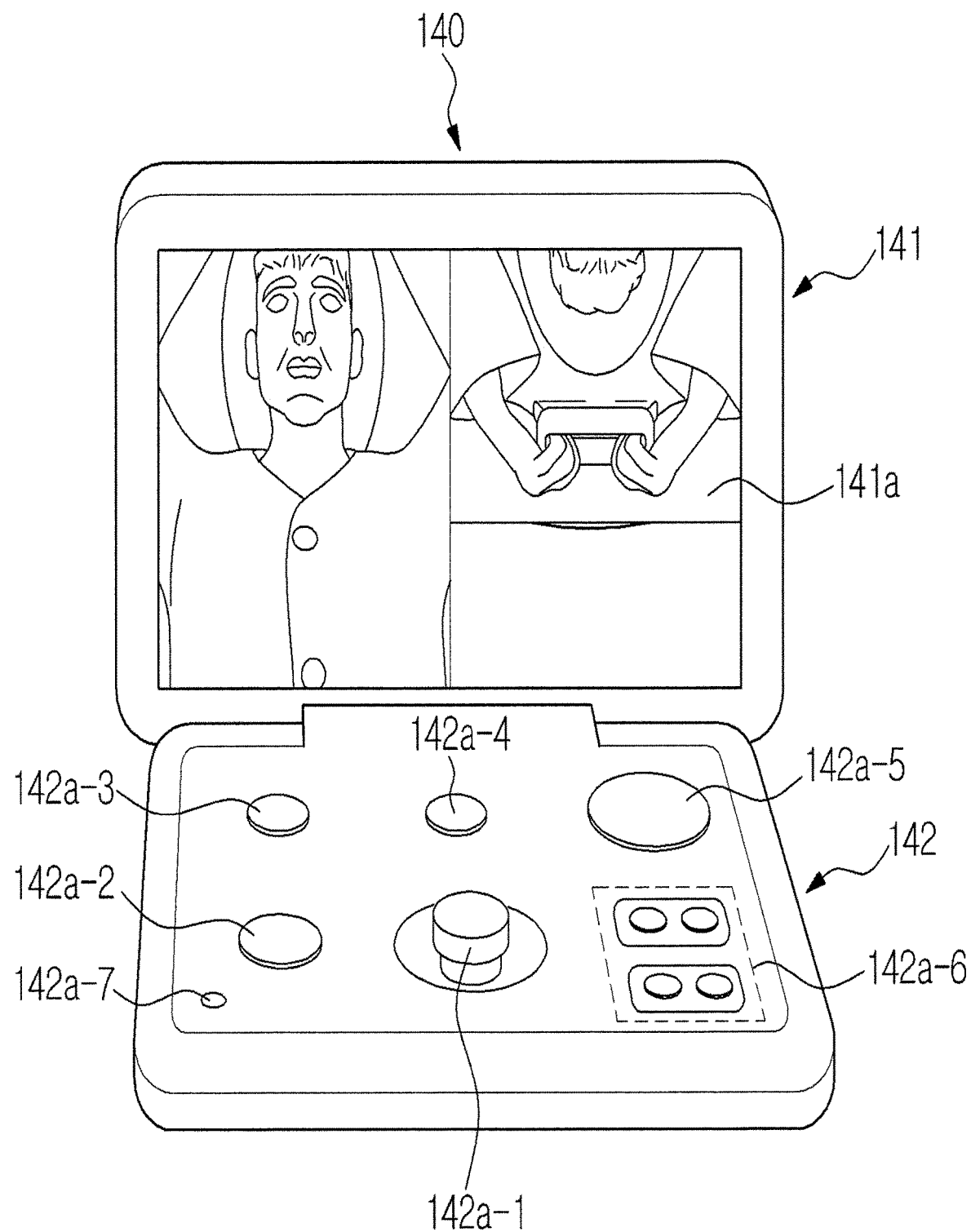

FIGS. 10A and 10B illustrate in detail an operation of moving the patient table using the control apparatus.

For scanning of the object, the object is placed on the patient table 153. The upper part or lower part of the object may be directed towards the scanner 110 according to a scan region of the object. In an exemplary embodiment, the upper part of the object is directed towards the scanner 110, and the imager 130 is mounted on each of the front surface and rear surface of the scanner 110.

Respective images captured by the imager 130 on the front surface and rear surface of the scanner 110 may be displayed on the display 141a of the mobile display device 141. In order to enable the user to monitor a situation at the front surface of the scanner 110 and a situation at the rear surface of the scanner 110 at a glance, the display 141a may be partitioned into two parts which display an image captured on the front surface of the scanner 110 and an image captured on the rear surface of the scanner 110, respectively. Although the display 141a is shown in FIGS. 10A and 10B as being partitioned into left and right parts, an exemplary embodiment is not limited thereto. For example, the display 141a may be partitioned into upper and lower parts.

The user monitors the position of the patient table 153 in real time while viewing the display 141a, and moves the patient table 153 into the bore 103 by pushing the table movement key 142a-1 forward. The movement of the patient table 153 may be checked on the display 141a. As a result, the user may move the patient table 153 to a desired position as shown in FIG. 10B by operating the table movement key 142a-1 while checking the movement amount of the patient table 153 on the display 141a.

Alternatively, the user may move the patient table 153 to a preset scan position at once by pushing the table movement key 142a-1 forward to the end.

Controlling the movement of the patient table 153 using the jog shuttle may make the movement direction of the patient table 153 equal to the movement direction of the jog shuttle, so that the user may intuitively control the patient table 153 with an improved sense of operation.

Upon completion of the movement of the patient table 153, the user may depress the scan start key 142a-2 to start scanning of the object. When the scan start key 142a-2 is depressed, a control command signal to start scanning is transmitted to the scan controller 121, which controls the scanner 110 to start the scan operation.

An image of the object captured by the imager 130 is displayed on the display 141a during the scan operation, so that the user may monitor the state of the object through the display 141a. For scanning, the object may take medicine such as a contrast agent. A side effect may be caused by the taken medicine according to the object. For this reason, the user monitors the state of the object while viewing the image of the object displayed on the display 141a. Upon determining that the object exhibits a side effect such as a vomiting or breathing difficulty, the user may depress the emergency stop key 142a-5 to stop the scan operation. When the emergency stop key 142a-5 is depressed, a control command signal for the stop of the scan operation is transmitted to the scan controller 121, which then controls the scanner 110 to stop the scan operation.

The state of the object may be monitored in various manners. However, a symptom such as vomiting or breathing difficulty may be checked by monitoring the face of the object which may be included in an image of the object captured by the imager 130. Provided that the imager 130 includes a face-tracking camera, it may automatically recognize, track and capture the face of the object. Alternatively, where the imager 130 includes a wide-angle camera covering the entire object, the face of the object may be captured irrespective of a scan region of the object.

For normal scanning of the object, it is required that the object does not move. For this reason, the user may determine whether the object moves, through an image of the object displayed on the display 141a, and perform a control operation based on a result of the determination.

Figure 11:
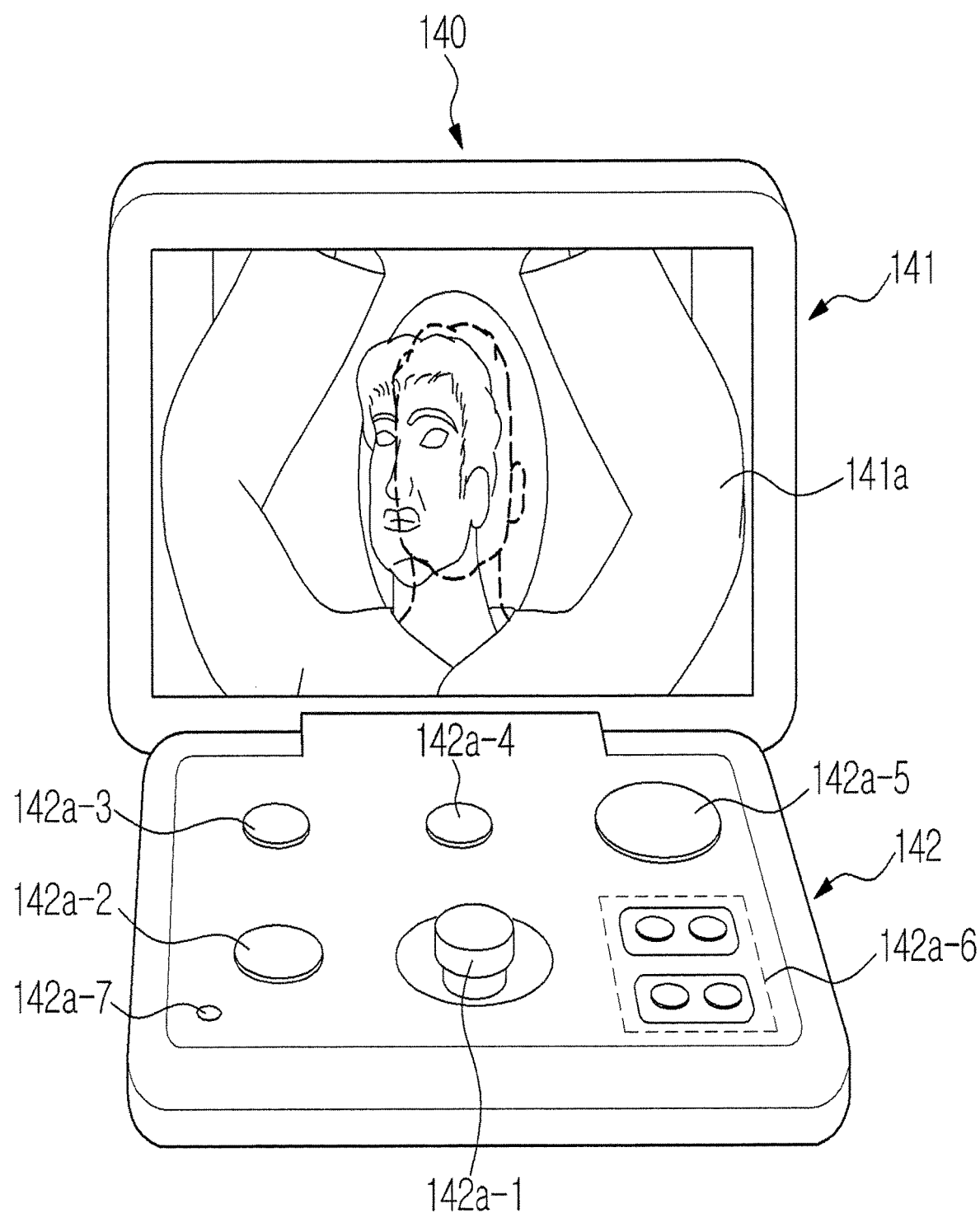
FIG. 11 is a view illustrating an operation of the control apparatus to determine whether an object moves.

FIG. 11 illustrates an operation of the control apparatus to determine whether the object moves.

Although the user may personally determine whether the object moves, the control apparatus 140 may automatically determine whether the object moves. The mobile controller 141c may store a motion recognition algorithm, and analyze an image of the object captured by the imager 130 based on the motion recognition algorithm to determine whether the object moves. Any known motion recognition algorithm is applicable to an exemplary embodiment.

When it is determined that the object moves, a warning may be given to the user in various manners. For example, as shown in FIG. 11, a position before the object moves may be marked with a dotted line or solid line and displayed on the display 141a together with the current image, the edge of the display 141a may be flickered with a red color, or a separate warning pop-up may be displayed on one area of the display 141a which does not screen the object. Alternatively, a warning may be audibly given through a speaker provided in the mobile display device 141.

Upon determining that the object moves, the user may depress the scan pause key 142a-3 to stop the scan operation, and input a voice requesting the object not to move, through the microphone 142a-7.

Figure 12:
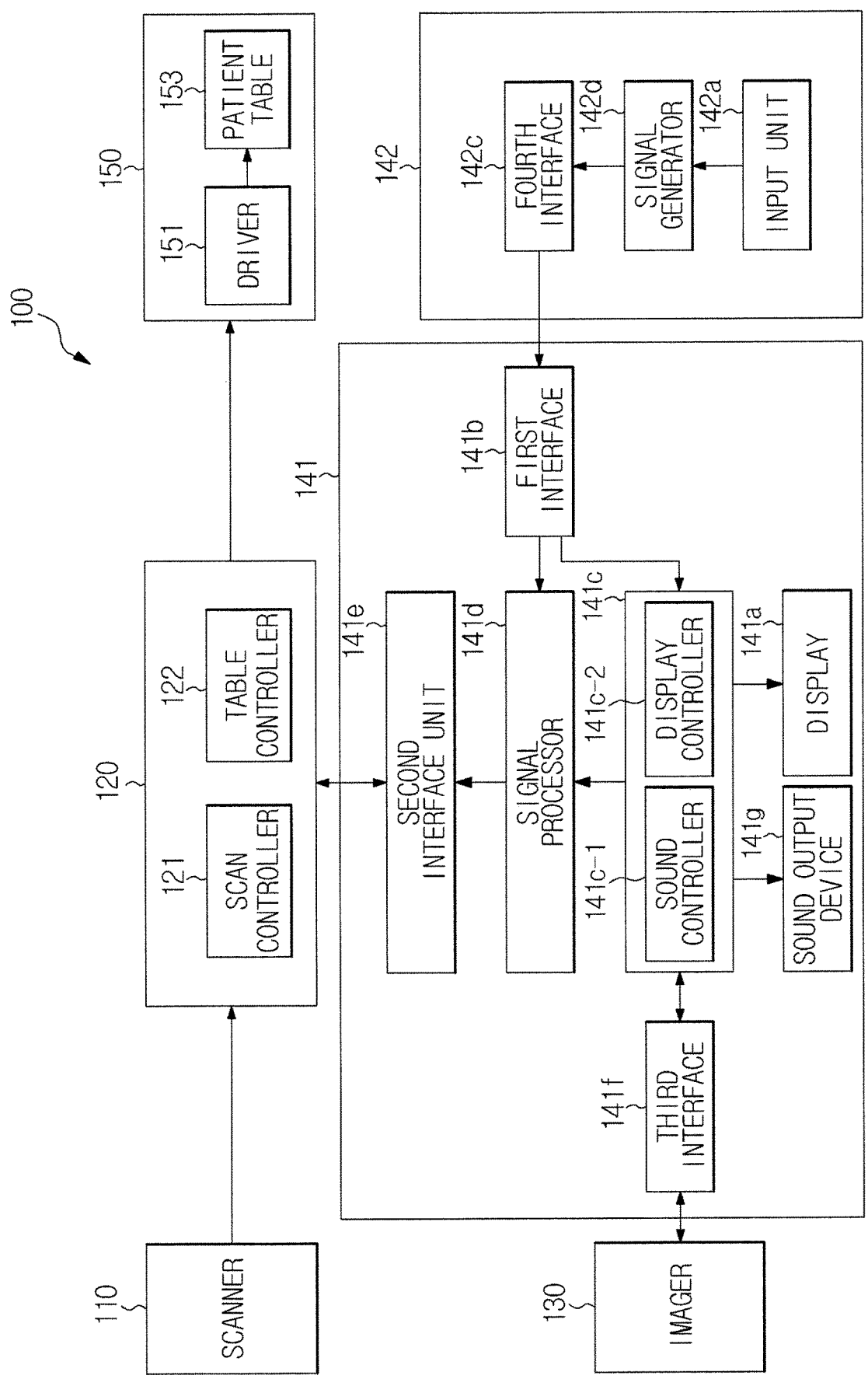
FIG. 12 is a detailed block diagram showing a sound output level adjustment configuration of the medical imaging apparatus.
Figure 13:
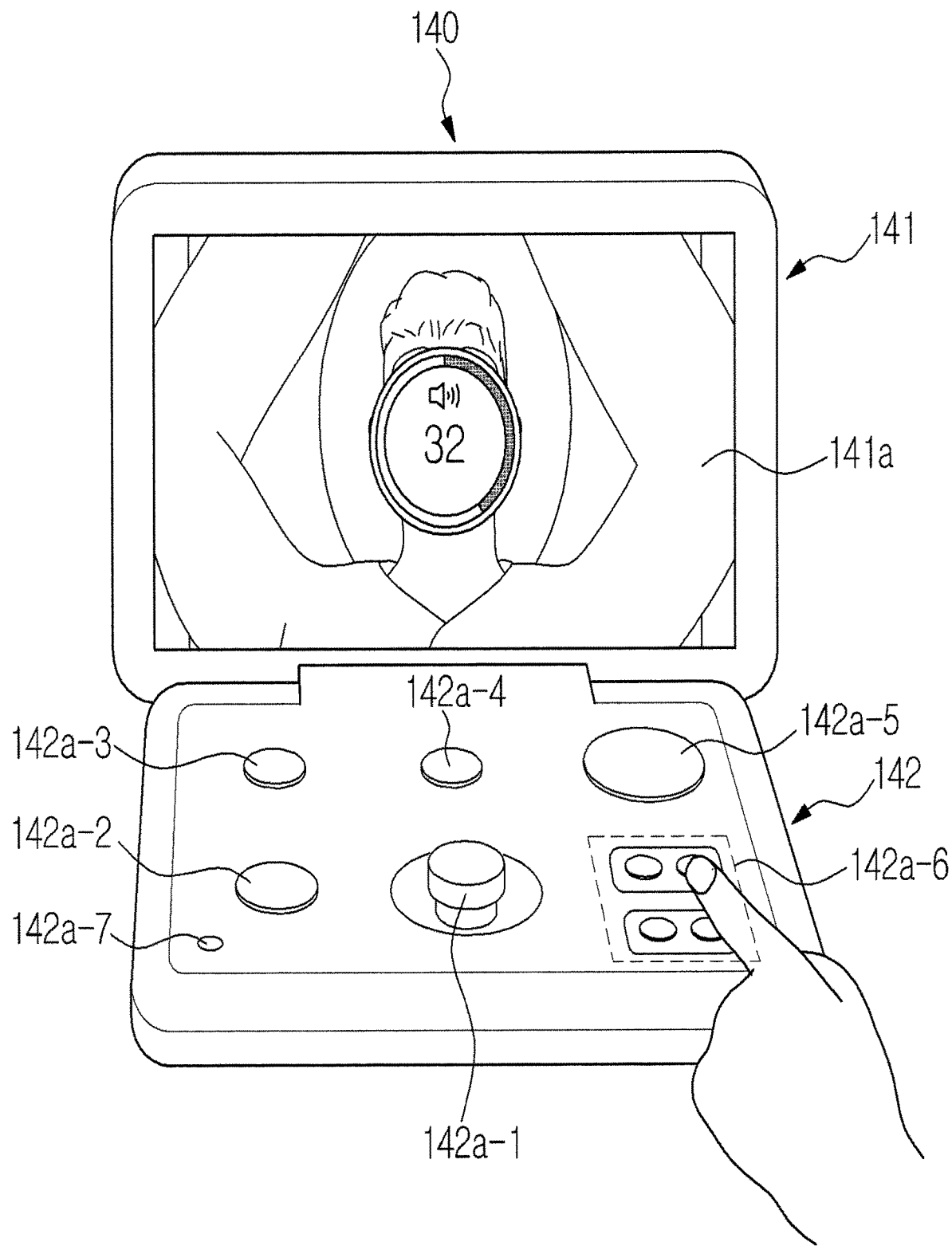
FIG. 13 is a view illustrating an operation of adjusting a sound output level using the control apparatus.

FIG. 12 is a detailed block diagram showing a sound output level adjustment configuration of the medical imaging apparatus, and FIG. 13 illustrates an operation of adjusting a sound output level using the control apparatus.

As needed, the user's voice may be output to the scan room or the object's voice may be output to the user. As shown in FIG. 12, the mobile display device 141 may include a sound output device 141g, and the mobile controller 141c may include a display controller 141c-2 to control the display 141a, and a sound controller 141c-1 to control the sound output device 141g. The sound output device 141g may include a device which outputs a sound, such as a speaker.

For example, for monitoring of the state of the object or conversation with the object, the object's voice may be output through the sound output device 141g provided in the mobile display device 141. A microphone capable of inputting the object's voice may be provided in the scan room, and a signal corresponding to the object's voice input through the microphone (referred to hereinafter as an object voice signal) may be transmitted to the mobile display device 141. The object voice signal may be transmitted to the mobile display device 141 through the second interface 141e or the third interface 141f. The sound controller 141c-1 processes the object voice signal and outputs the processed signal as an audible sound, for example, voice, through the sound output device 141g.

Referring to FIG. 13, a control command for a sound output level may be input through the sound level key 142a-6 provided in the input device 142. In the illustration of FIG. 13, when the user depresses one of upper keys of the sound level key 142a-6, the signal generator 142d senses the key depression, generates a corresponding control command signal and transfers the generated control command signal to the mobile display device 141 through the fourth interface 142c. The sound controller 141c-1 of the mobile display device 141 adjusts the level of a sound output through the sound output device 141g in response to the transferred control command signal.

For example, to provide guidance for scanning to the object or check the state of the object, the user may output his/her voice through a speaker provided in the scan room. In this case, when the user's voice is input through the microphone 142a-7 provided in the input device 142, the signal generator 142d generates a signal corresponding to the input user's voice (referred to hereinafter as a user voice signal) and transmits the generated user voice signal to the controller 120 through the mobile display device 141. The controller 120 may have a function of controlling the speaker provided in the scan room, and outputs the transmitted user voice signal through the speaker provided in the scan room.

A control command for a sound output level may be input through the sound level key 142a-6. In FIG. 13, when the user depresses one of lower keys of the sound level key 142a-6, the signal generator 142d senses the key depression, generates a corresponding control command signal and transfers the generated control command signal to the mobile display device 141 through the fourth interface 142c. The mobile display device 141 transmits the transferred control command signal to the controller 120 to adjust the level of a sound output through the speaker provided in the scan room, as schematically illustrated by a digit "32".

Although the input unit 142a of the input device 142 has been described in an exemplary embodiment as being implemented in the button manner, it may be implemented in the touch manner. Hereinafter, the implementation of the input unit 142a in the touch manner will be described.

Figure 14:
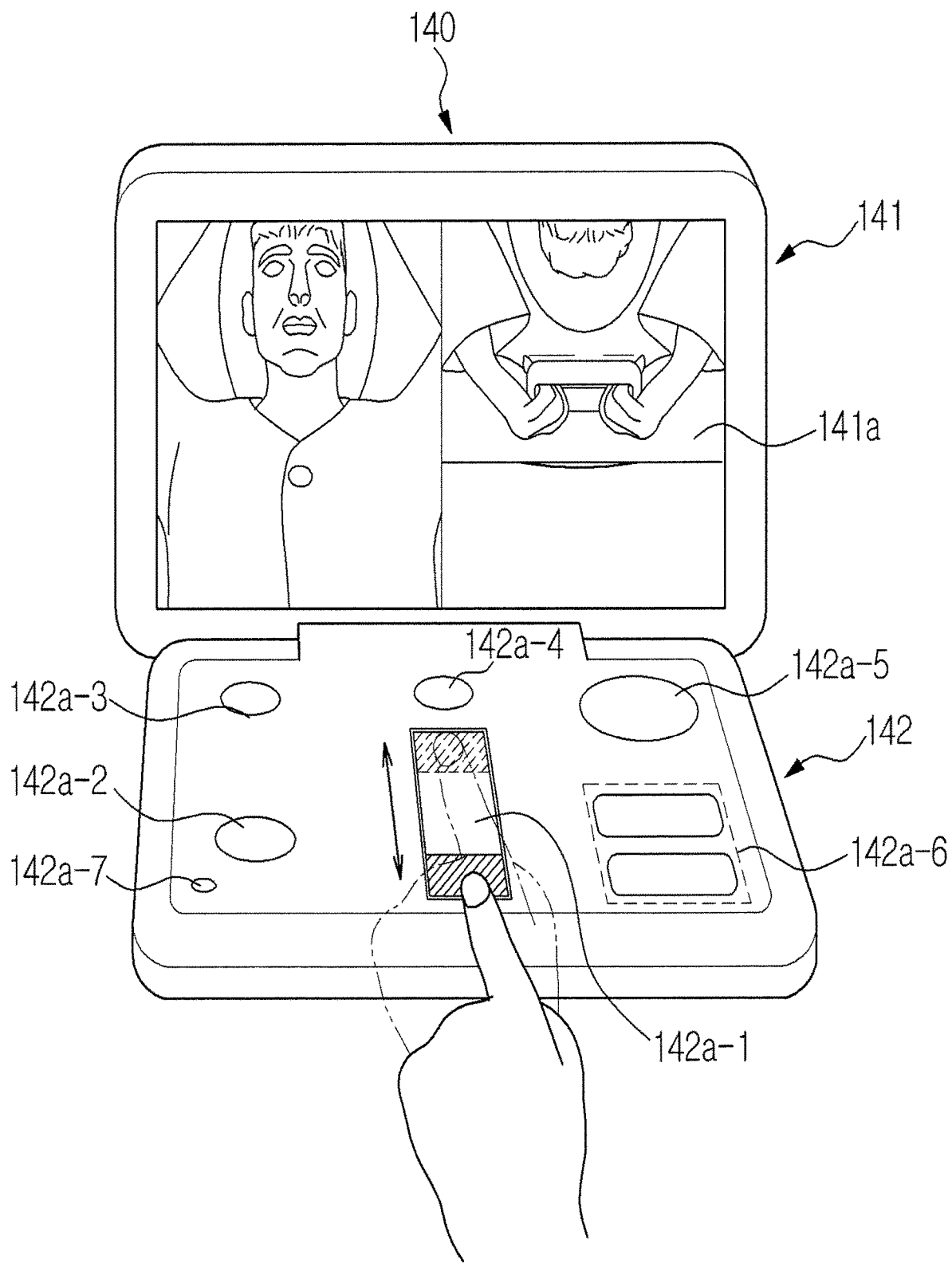
FIG. 14 is a view showing the outer appearance of the control apparatus in which the input unit is implemented in a touch manner.
Figure 15:
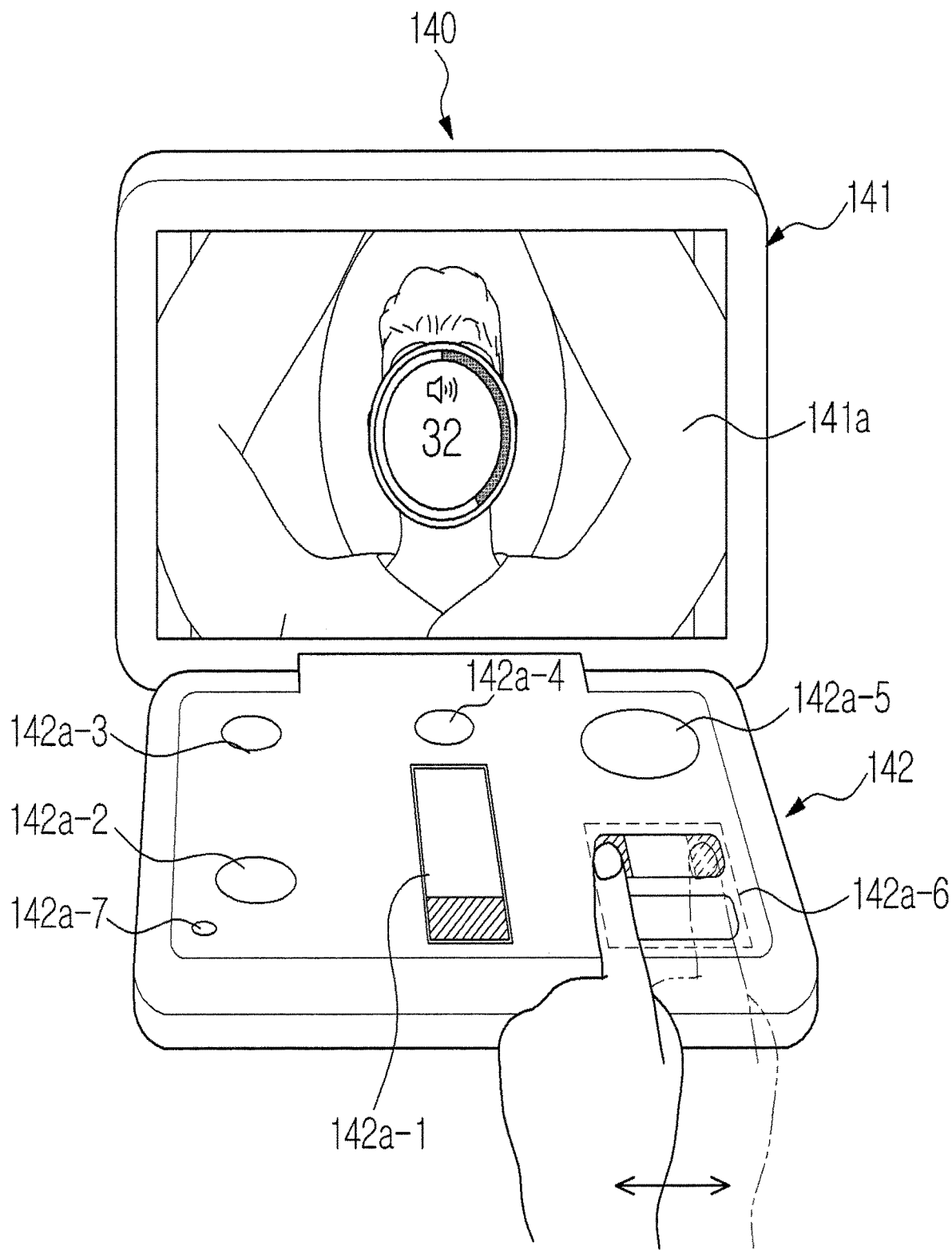
FIG. 15 is a view showing the outer appearance of the control apparatus in which the input unit is implemented in a touch manner.

FIGS. 14 and 15 show the control apparatus in which the input unit is implemented in the touch manner.

Referring to FIG. 14, the input unit 142a of the input device 142 may input a control command in the touch manner and may include a touch panel implemented by a resistive technology (or pressure-sensitive technology) which senses pressure, a capacitive technology which senses static electricity generated from a human body, an ultrasonic technology which emits ultrasonic waves onto the surface of a panel, and/or an infrared technology which arranges a plurality of infrared sensors around a panel to sense interception of an infrared ray at a touched position. The input unit 142a is not limited in touch sensing technology, and any of the above technologies is applicable to the input unit 142a.

As an example, the table movement key 142a-1 may be shaped as a bar which is movable back and forth within a certain area. Touching the table movement key 142a-1 and dragging it forward, in a direction toward the display, may perform the same function as forward pushing the jog shuttle, as described with reference to FIGS. 9 and 10. As a result, when the user touches the table movement key 142a-1 and drags it forward, the patient table 153 is moved toward the scanner 110. The patient table 153 may be moved by a drag amount of the table movement key 142a-1.

The sound level key 142a-6 may be shaped as a bar or bars which are movable right and left within a certain area, as shown in FIG. 15. Touching the sound level key 142a-6 and dragging it right and left may perform the same function as depressing the upper and lower keys of the sound level key 142a-6, described with reference to FIGS. 12 and 13. As a result, the level of a sound output through the sound output device 141g or the speaker provided in the scan room may be increased when the user touches one of the bar-shaped keys of the sound level key 142a-6 and drags it right, and decreased when the user touches the sound level key 142a-6 and drags it left.

Although the input unit 142a is shown in FIG. 15 as having the same configuration as that when it is implemented in the button manner described above, an exemplary embodiment is not limited thereto. For example, the input unit 142a, which includes the touch panel, may have a variable layout, which may be optimized to the user. That is, the configuration of the input unit 142a displayed on the touch panel may be set and changed by the user. As an example, keys for functions mainly used may be provided as default keys, and keys for other functions may be designated by the user. In addition, the user may call a function of a high frequency of use by virtue of a hot key.

The display 141a may include a touch screen, which recognizes a touch signal, and a control command from the user may be input through the display 141a. When the control command is input through the touch screen, the display controller 141c-2 may generate a corresponding control command signal and transmit the generated control command signal to the imager 130, the controller 120, and/or the scanner 110.

Figure 16:
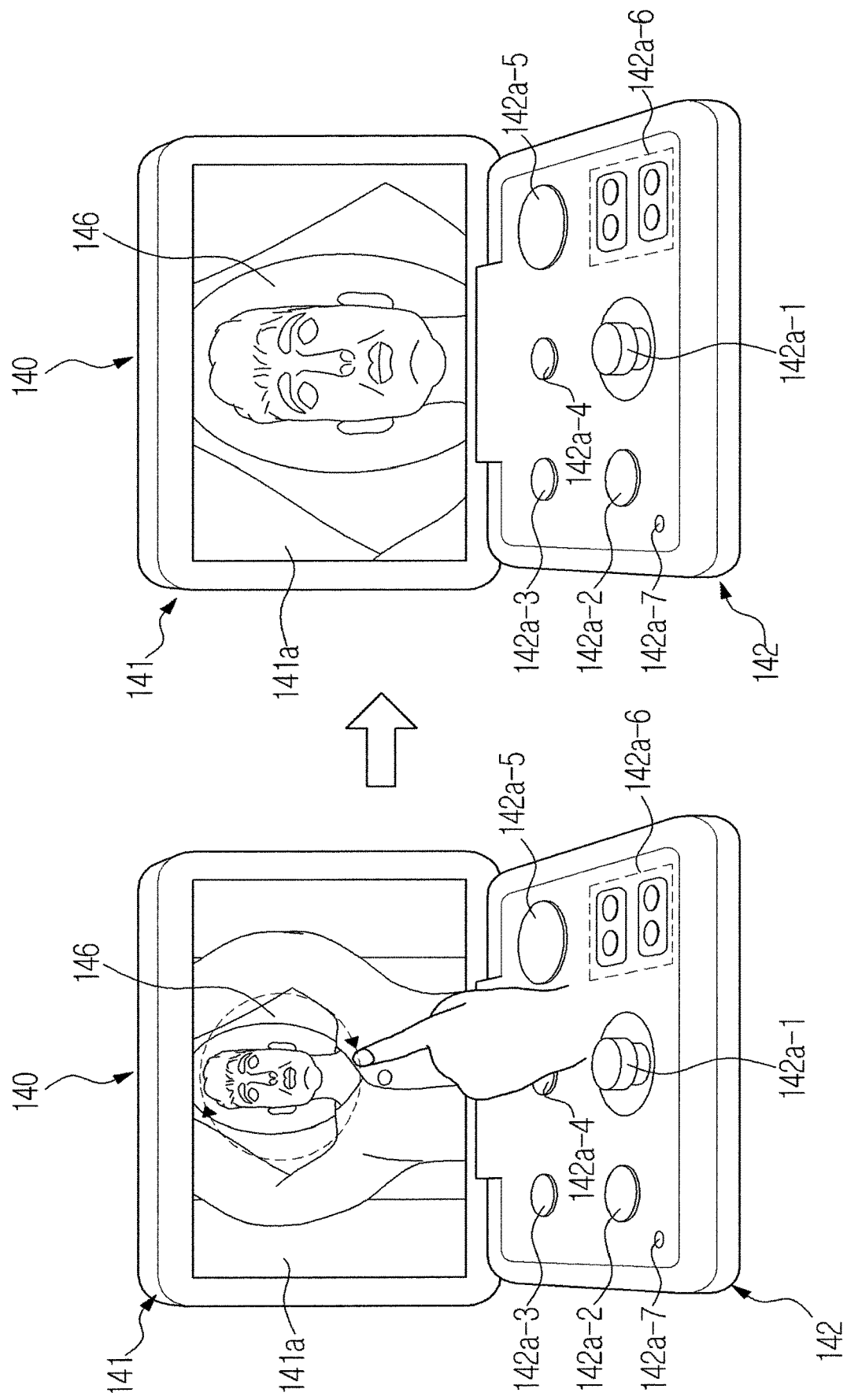
FIG. 16 is a view illustrating an operation of controlling a zoom function of the imager using the control apparatus.

FIG. 16 illustrates an operation of controlling a zoom function of the imager using the control apparatus.

As an example, the user may input a region of interest (ROI) 146 by touching the display 141a on which an image of the object is displayed, as shown in FIG. 16. The display controller 141c-2 may generate a control command signal including information about the ROI 146 and transmit the generated control command signal to the imager 130 through the third interface 141f. The imager 130 may zoom in the ROI 146 input by the user.

There is no limitation as to input of the ROI by the user. The user may drag a circular area whose center is aligned with the center of the ROI 146, such that the imager 130 zooms in on the center of the dragged area, as shown in FIG. 16. The user may drag a polygonal area such as a rectangular area or triangular area, besides the circular area. Alternatively, the user may touch the center of the ROI. A magnification at which the imager 130 zooms in at once may be preset, or may be changed by the user.

On the other hand, provided that the user drags the contour or boundary of the ROI, the capturing range of the imager 130 may be limited to the contour or boundary of the ROI. That is, the user may input the ROI itself through dragging, not the center of the ROI. In this case, the imager 130 may zoom in irrespective of a preset magnification.

Therefore, the user may rapidly zoom in the ROI to monitor the state of the object, so as to cope with an abnormal sign of the object at an early stage.

On the other hand, although the sound output level has been described with reference to FIGS. 13 and 15 as being controlled through the sound level key 142a-6 the input unit 142a, it may be controlled through the display 141a which includes a touch screen. In detail, the user may input a control command for the sound output level by touching a sound level icon displayed on the display 141a or dragging the contour of the sound level icon, similarly to what is described above.

The control apparatus 140 may further perform various functions in addition to the above-described functions. A detailed description will hereinafter be given of additional functions of the control apparatus 140.

Figure 17:
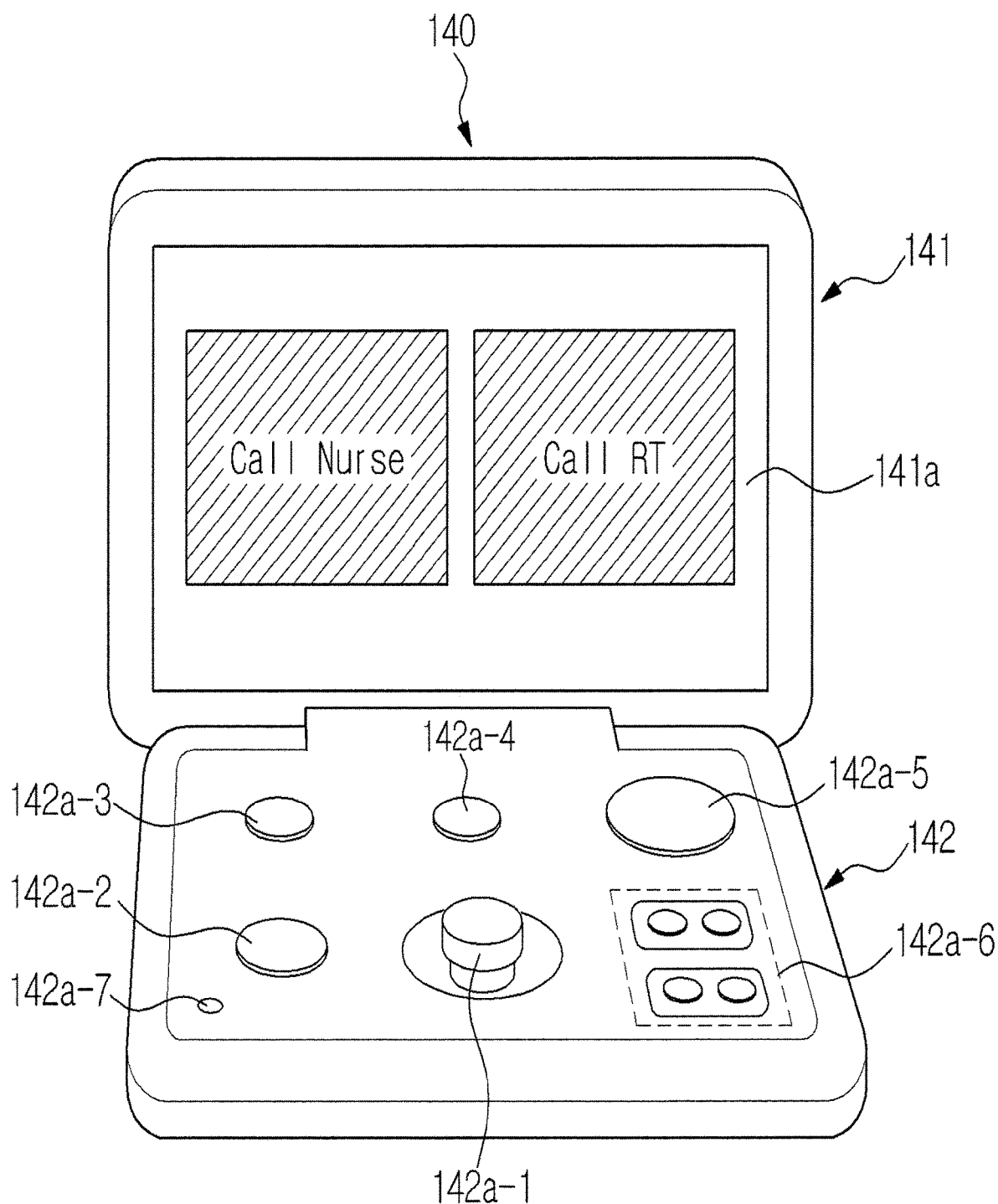
FIG. 17 is a view illustrating display of an emergency call menu on a display.
Figure 18:
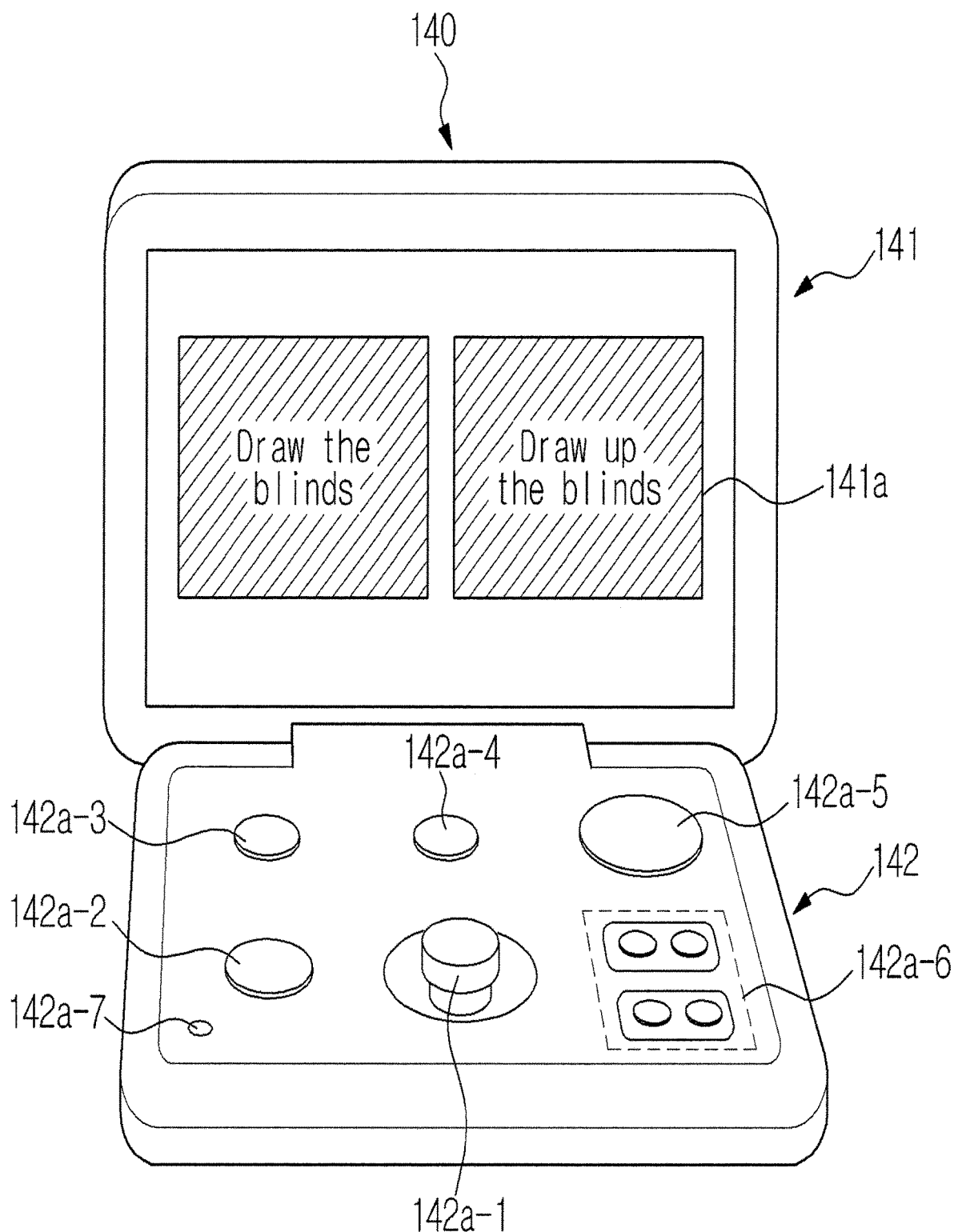
FIG. 18 is a view illustrating display of a blind control menu on the display.
Figure 19:
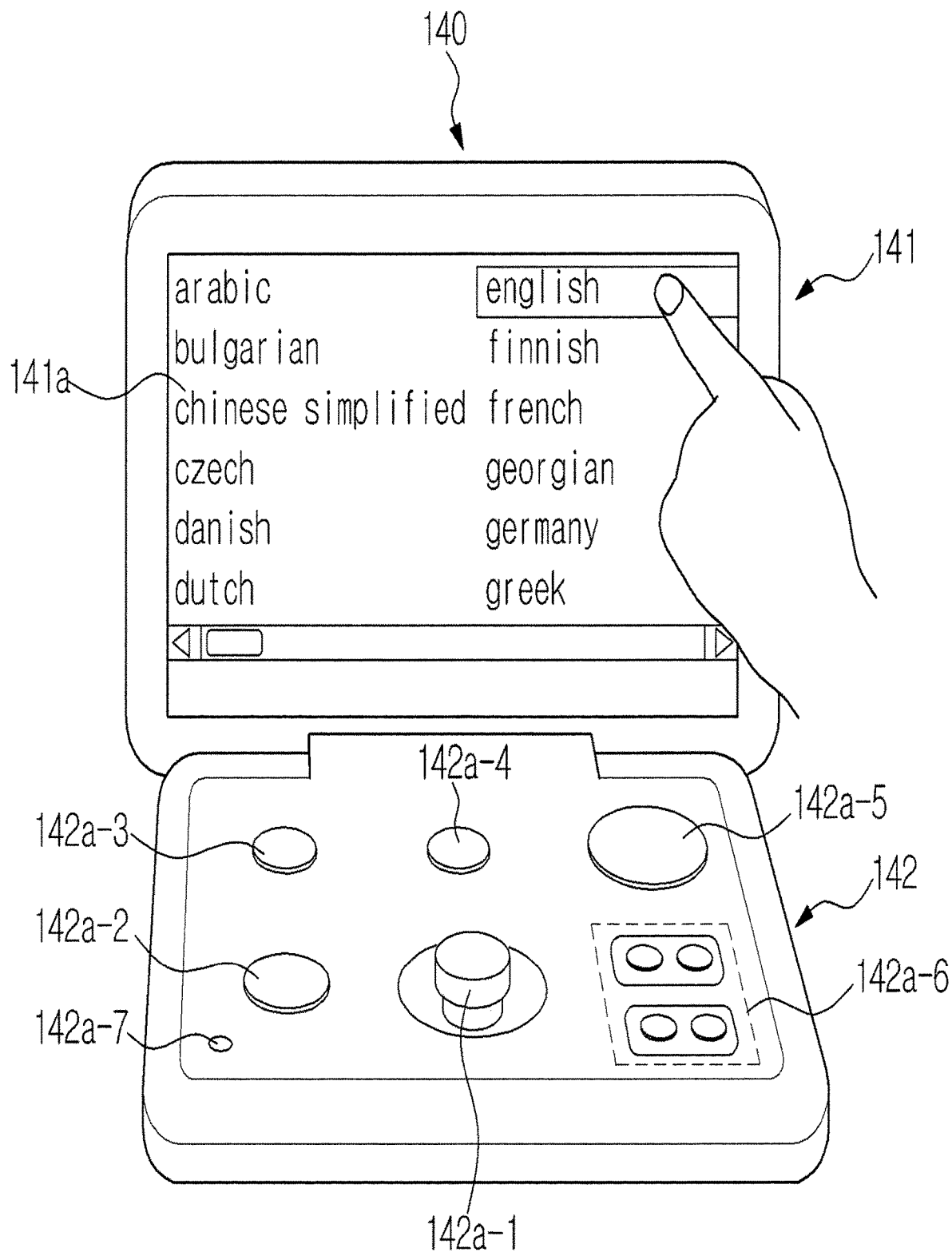
FIG. 19 is a view illustrating display of a screen for selection of a language of a breathing guide provided to the object on the display.

FIG. 17 illustrates display of an emergency call menu on the display, FIG. 18 illustrates display of a blind control menu on the display, and FIG. 19 illustrates display of a screen for selection of a language of a breathing guide provided to the object on the display.

For example, a menu Call Nurse for a nurse call and a menu Call RT for a respiratory therapist (RT) call may be displayed on the display 141a, as shown in FIG. 17. When at least one of the two menus is selected by the user, a nurse or RT may be called through a communication network in a hospital. The menu selection may be made by touching the display 141a or operating a key provided in the input device 142. In addition, the mobile display device 141 may call the nurse or RT directly through the communication network in the hospital, or transmit a call signal to the controller 120 such that the controller 120 calls the nurse or RT through the communication network in the hospital.

The object may take off the clothes for scanning depending on a scan region. In this case, blinds mounted on the shield glass may be drawn for protection of the object's privacy. The user performing a control operation on the work table may move to personally draw the blinds. In this case, work efficiency may be degraded. For this reason, the blinds mounted on the shield glass may be implemented in an electric manner such that they are automatically controlled by the user.

The blind control menu may be displayed on the display 141a, as shown in FIG. 18. When the user selects a blind drawing down operation or blind drawing up operation by touching the display 141a or operating a key provided in the input device 142, the mobile display device 141 may transmit a control command signal to the blinds to draw down or up.

For scanning, the object may have to breathe according to a guide, i.e., in a preset manner. A breathing guide may be provided to the object. For example, the breathing guide may be explained personally by the user or provided to the object on paper. Explaining the breathing guide personally by the user may increase a work burden of the user. Particularly, when the object is a foreigner, separate staff capable of speaking a corresponding foreign language may be necessitated. In the case where the breathing guide is provided on paper, it may be lost and be difficult to effectively provide.

Therefore, the mobile display device 141 stores breathing guide images by languages, and displays a language selection menu on the display 141a, as shown in FIG. 19. The user may select a desired language by touching the display 141a or operating a key provided in the input device 142, and a breathing guide image of the selected language is displayed on the display 141a.

Because the mobile display device 141 is freely detachably mounted with the input device 142, the user may take the mobile display device 141 to the object to provide the breathing guide to the object as an image of a language suitable to the object. Alternatively, a display device may be mounted on one side of the scanner 110, and a breathing guide image of a language selected in the mobile display device 141 may be displayed through the display device mounted on the scanner 110.

Although the mobile display device 141 and the input device 142 are shown in FIGS. 16 to 19 as being docked with each other, they may be undocked from each other and a control command from the user may be input through the display 141a having a touch screen.

The control apparatus 140 may perform various other functions. For example, the control apparatus 140 may display a user manual through the display 141a, or may be operatively coupled with the controller 120 to display a scan image of the object or be operatively coupled with a picture archiving communication system (PACS).

When the mobile display device 141 and the input device 142 are docked with each other while specific information is displayed through the display 141a under the condition that the mobile display device 141 and the input device 142 are undocked from each other, a mode selection menu may be displayed through the display 141a or a change to a specific mode may be made, irrespective of whether the display 141a is implemented with a touch screen.

As an example, when the mobile display device 141 and the input device 142 are docked with each other while an image of the object is displayed through the display 141a, a change to a table control mode may be made. If the change to the table control mode is made, a signal transferred from the input device 142 is recognized as a control command signal for the movement of the patient table 153, and the movement of the patient table 153 is controlled based on the control command signal.

As another example, when the mobile display device 141 and the input device 142 are docked with each other while a breathing guide image is displayed through the display 141a, an image of the object may be displayed.

As another example, when the mobile display device 141 and the input device 142 are docked with each other while an image of the object or a breathing guide image is displayed through the display 141a, the mode selection menu may be displayed.

Figure 20:
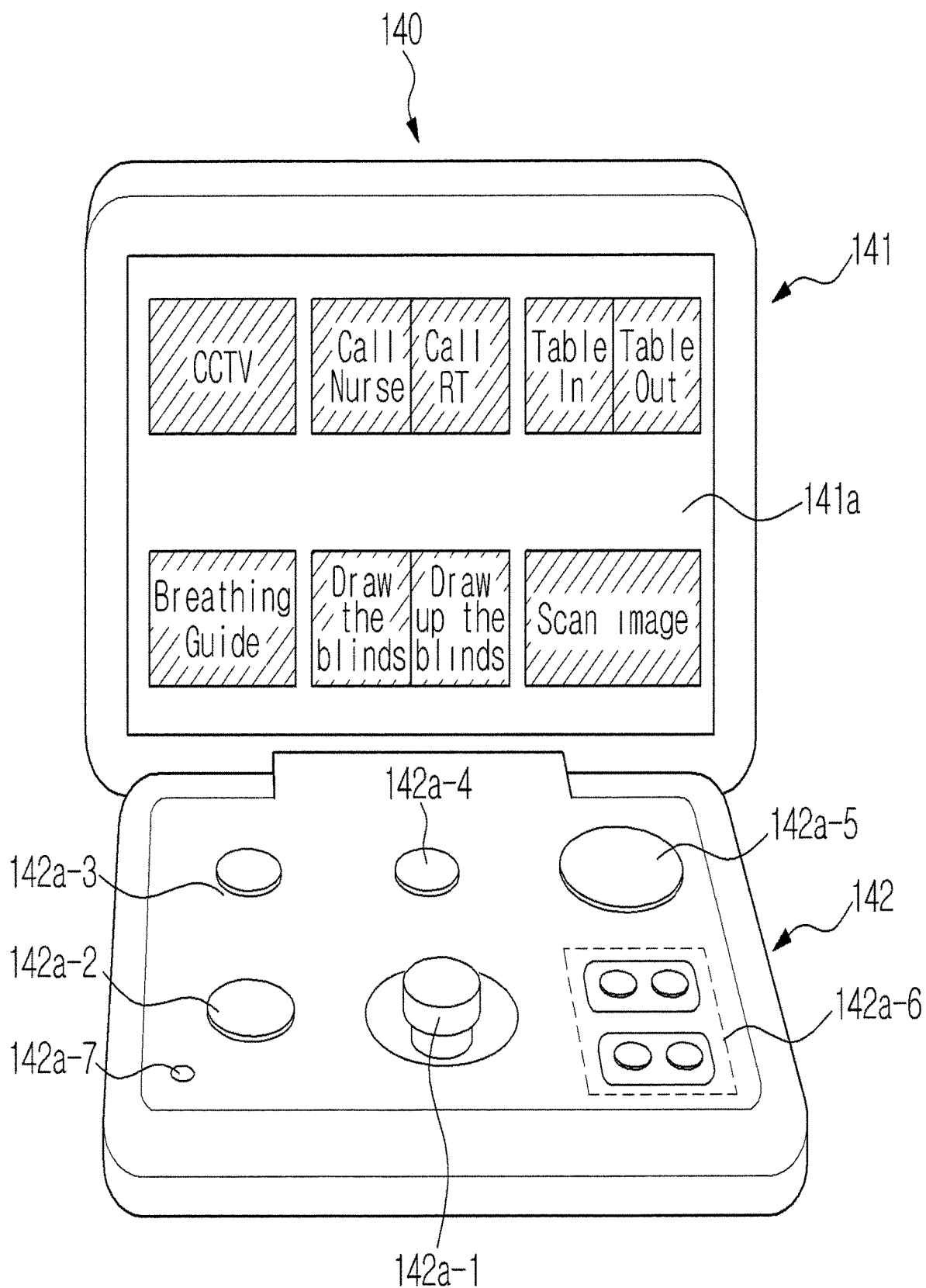
FIG. 20 is a view illustrating display of a mode selection menu on the display.

FIG. 20 illustrates display of the mode selection menu on the display.

When the mobile display device 141 and the input device 142 are docked with each other, the mode selection menu may be displayed, which includes a mode CCTV to display an image of the object, call modes Call Nurse/Call RT to cope with an emergency, blind control modes Draw the blinds/Draw up the blinds, a scan image display mode Scan image, table control modes Table in/Table out, and a breathing guide image display mode Breathing Guide, as shown in FIG. 20. Here, the call modes Call Nurse/Call RT, the blind control modes Draw the blinds/Draw up the blinds, and the table control modes Table in/Table out may be simultaneously displayed on a mode selection screen so that they may be directly controlled on the mode selection screen, as shown in FIG. 20. Alternatively, only a call menu Call, a blind control menu Blind and a table control menu Table may be displayed, and sub-menus may be displayed when a corresponding one of the menus is selected.

The screen shown in FIG. 20 may become a home screen which is displayed upon power-on of the mobile display device 141.

Although the imager 130 is described above as being mounted on the scanner 110, it may include a CCTV installed in the scan room, as described below in detail.

Figure 21:
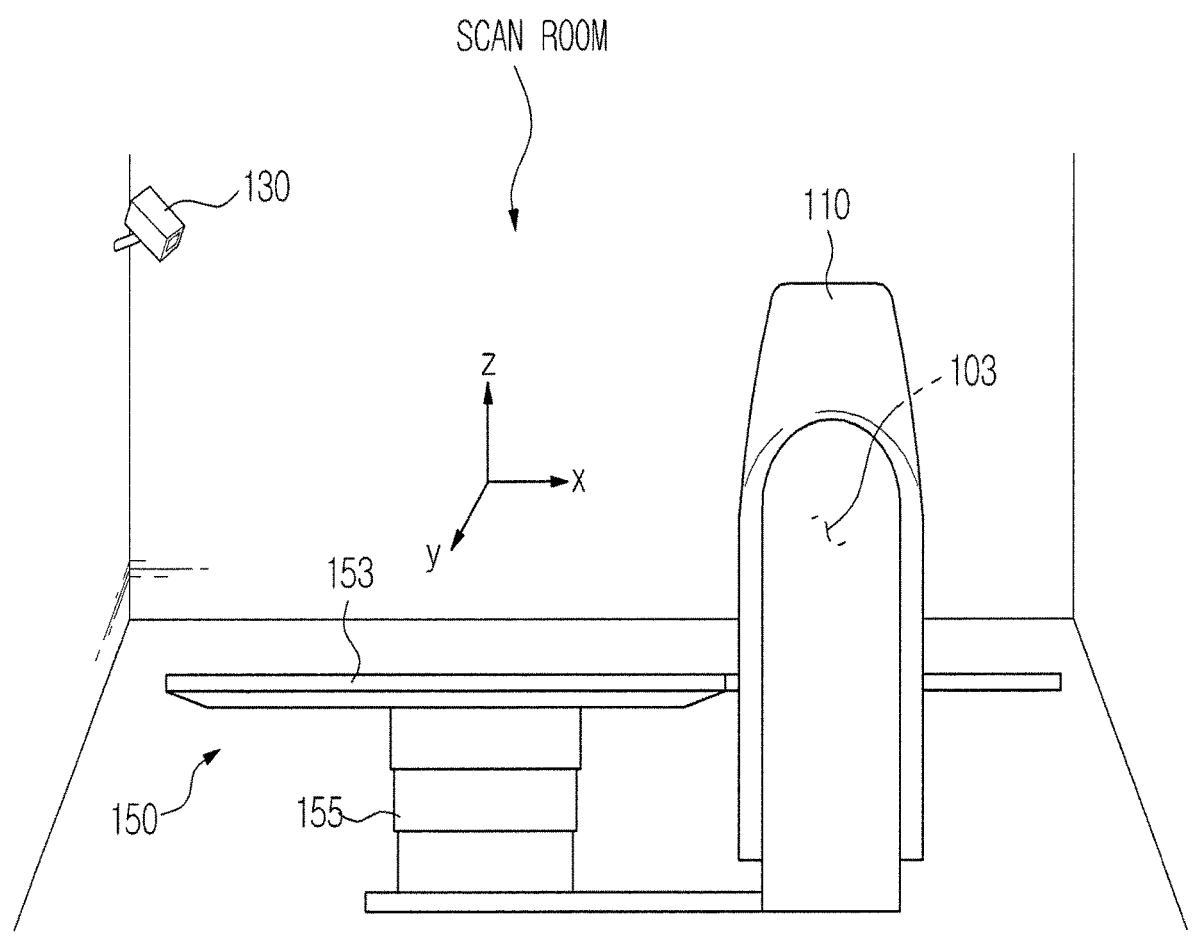
FIG. 21 is a view showing a scan room in which the scanner of the medical imaging apparatus is located.

FIG. 21 shows the scan room in which the scanner of the medical imaging apparatus is located.

Referring to FIG. 21, the scanner 110 and patient table assembly 150 of the medical imaging apparatus 100 are located in the scan room, and the imager 130 is mounted on the inner wall of the scan room. The imager 130 may include a device capable of capturing and transmitting a moving image in real time, such as a CCTV. A position at which the imager 130 is mounted is not limited to a position of FIG. 21, and the imager 130 may be mounted at any position so long as it can capture an image of the object or an image including the object and the patient table 153.

Figure 22:
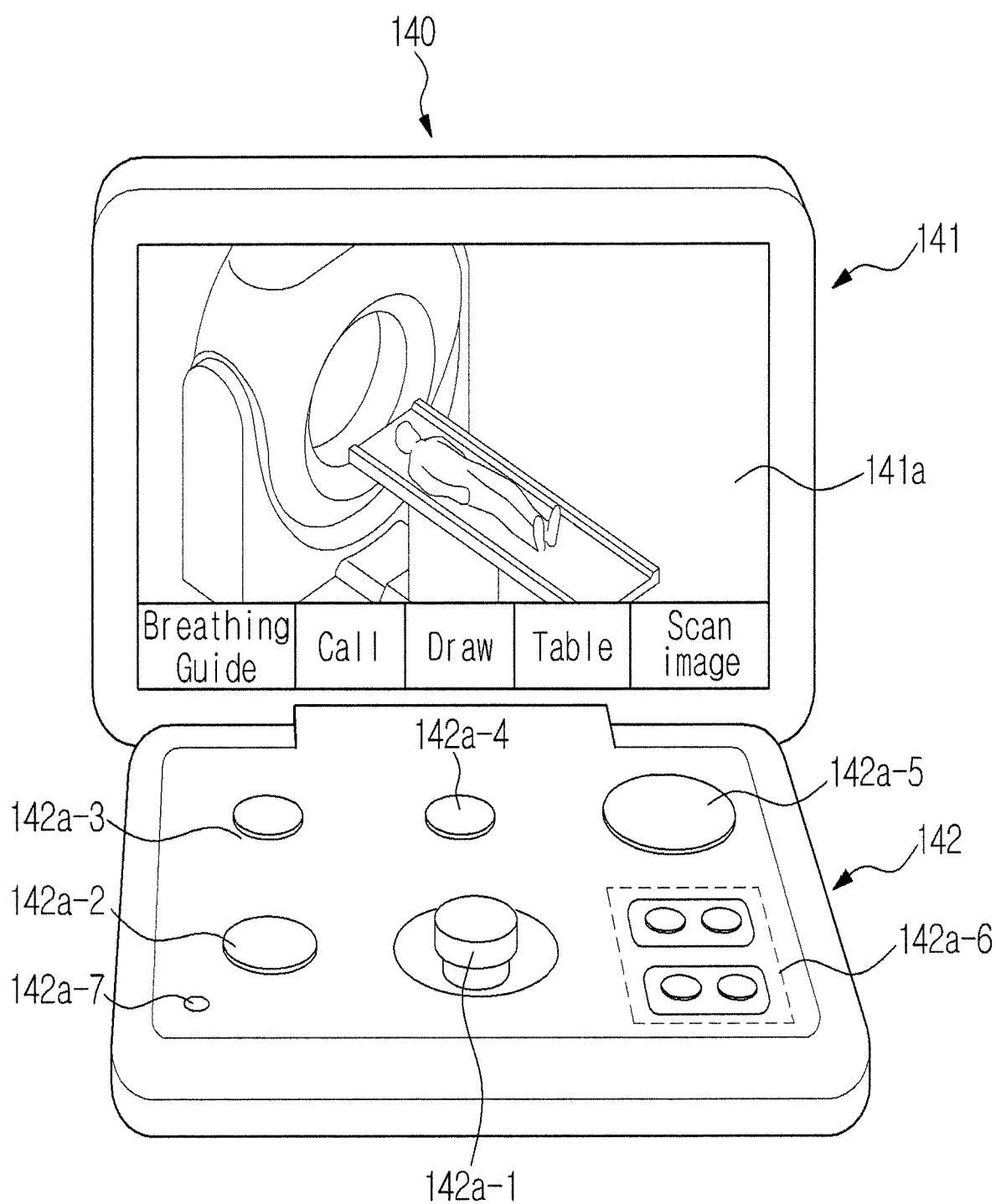
FIG. 22 and is a view illustrating display of an image of the object on the control apparatus.
Figure 23:
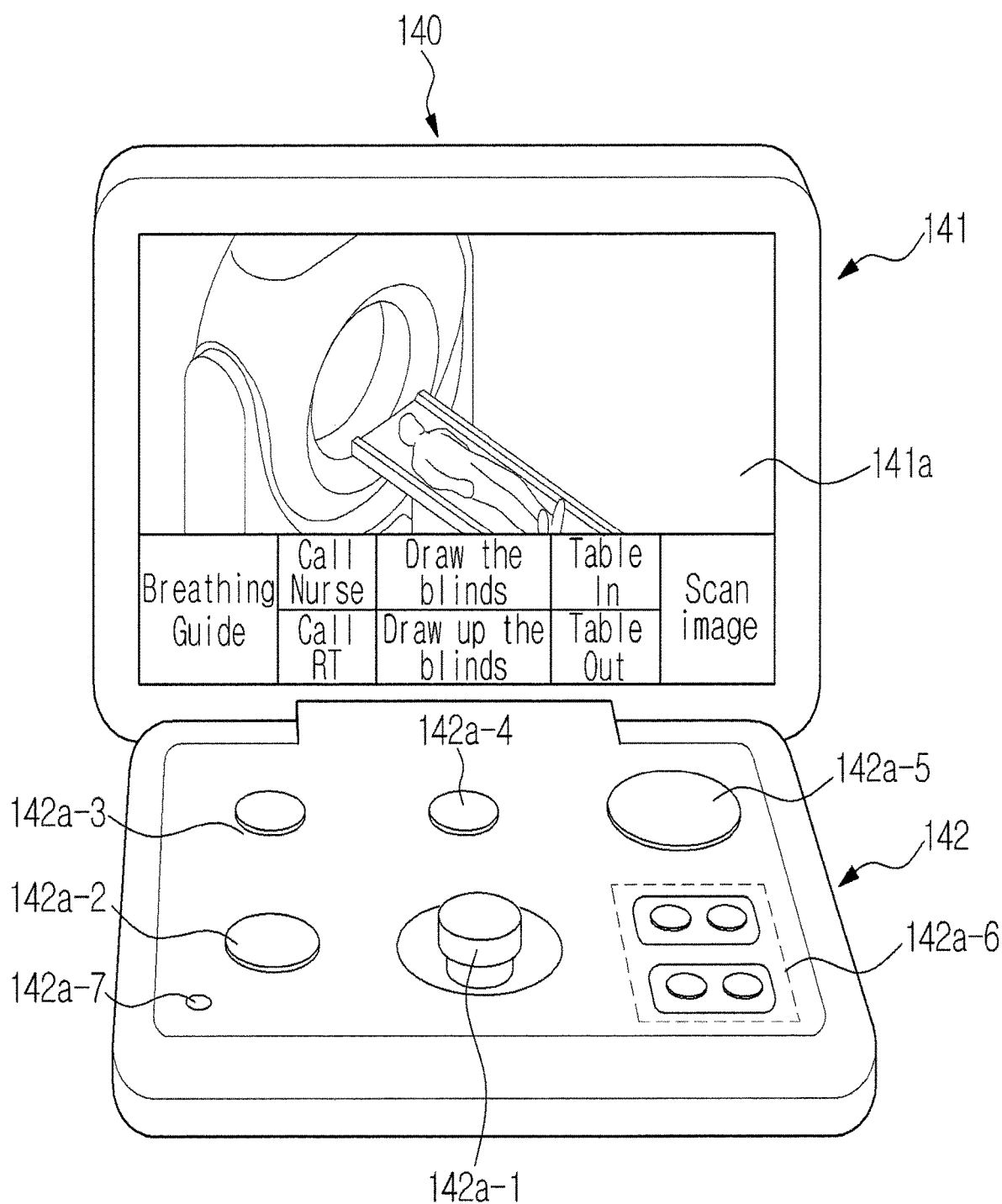
FIG. 23 is a view illustrating display of an image of the object on the control apparatus.

FIGS. 22 and 23 illustrate display of an image of the object on the control apparatus.

The imager 130 captures an image of the object and transmits the captured image to the mobile display device 141, which displays the image of the object through the display 141a as shown in FIG. 22. A mode selection menu may be displayed on side portion of the display 141a. As an example, the mode selection menu may include a breathing guide image display mode Breathing Guide, an emergency call mode Call, a blind control mode Blind, a table control mode Table, and a scan image display mode Scan image, as shown in FIG. 22.

When a mode selection is input from the user during the display of the image of the object through the display 141a, a corresponding one of the menus shown in FIGS. 17 to 19 may be displayed on the display 141a and a control operation corresponding to a corresponding mode may be performed.

On the other hand, a call menu, a blind control menu and a table control menu may be minutely displayed so that corresponding control operations may be performed under the condition that the image of the object is displayed. Referring to FIG. 23, the mode selection menu is displayed on one side of the display 141a on which the image of the object is displayed, and the call menu may be displayed, divided into menus Call Nurse and Call RT. The blind control menu may be displayed, divided into menus Draw the blinds and Draw up the blinds, and the table control menu may be displayed, divided into menus Table in and Table out. While viewing the image of the object displayed through the display 141a, the user may select a menu of a mode to be controlled and immediately perform a control operation associated with the selected mode.

As apparent from the above description, in a control apparatus and a medical imaging apparatus having the same according to an aspect of the present invention, an image indicative of the state of a patient is displayed on a mobile display device and a control command for an operation associated with the medical imaging apparatus is input through an input device docked with the mobile display device, so that the user may monitor the state of the patient in real time and perform a proper control operation based on the monitoring.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:
1. A computed tomography (CT) system comprising:
   a gantry comprising a bore and configured to scan an object to acquire CT image data of the object;
   a patient table configured to convey the object to the gantry;

an imager configured to capture an image of the object on the patient table;

a controller configured to control the patient table;

a portable user input device comprising at least one button configured to receive a user input for controlling the patient table, the controlling of the patient table comprising automatically aligning the object with a center of the bore;

a mobile display device connectable to the portable user input device, comprising a touch screen, and configured to:

in response to the portable user input device being connected to the mobile display device, display the image captured by the imager and make a change to a table control mode in which the mobile display device is operated to receive a control command corresponding to the user input for controlling the patient table from the portable user input device, and to transmit the control command to the controller, and in response to a user selection for a region of interest (ROI) being received by the touch screen while displaying the image captured by the imager, control the imager to zoom in the ROI, wherein the controller is configured to, based on the control command for aligning the object with the center of the bore, control the patient table so that the patient table is set to automatically align the object with the center of the bore, based on the image captured by the imager.

2. The CT system of claim 1, wherein the control command comprises a control command for laterally setting the patient table to laterally align the object with the center of the bore; and the controller is further configured to, based on the control command for laterally setting the patient table being obtained via the mobile display device, control the patient table so that the patient table is laterally set to laterally align the object with the center of the bore, based on the image captured by the imager.

3. The CT system of claim 1, wherein the controller is further configured to control the patient table so that the patient table is laterally set to laterally align the object with the center of the bore, based on a position of the object in the image captured by the imager.

4. The CT system of claim 1, wherein the at least one button comprises a hardware portion, and the control command for automatically aligning the object with the center of the bore is obtained via a pressing down of the hardware portion.

5. The CT system of claim 1, wherein the mobile display device is further configured to display a plurality of information for guiding an acquisition of the CT image data of the object.

6. The CT system of claim 1, wherein the portable user input device and the mobile display device are configured to be coupled by wire or wirelessly, wherein the mobile display device is further configured to:

display the image captured by the imager in a state in which the mobile display device and the portable user input device are uncoupled from each other, and based on the portable user input device and the mobile display device becoming coupled while the image captured by the imager is displayed, display a mode selection menu.

7. The CT system of claim 1, wherein the portable user input device and the mobile display device are configured to be coupled by wire or wirelessly, wherein the mobile display device is further configured to:

display a breathing guide image in a state in which the mobile display device and the portable user input device are uncoupled from each other, and based on the portable user input device and the mobile display device becoming coupled while the breathing guide image is displayed, display the image captured by the imager.

8. A method for acquiring computed tomography (CT) image data of an object, the method comprising:

controlling an imager to capture an image of the object on a patient table for conveying the object to a gantry, wherein the gantry is for scanning the object to acquire the CT image data of the object;

receiving, through at least one button of a portable user input device, a user input for controlling the patient table, the controlling of the patient table comprising automatically aligning the object with a center of a bore of the gantry;

in response to the portable user input device being connected to a mobile display device connectable to the portable user input device, controlling the mobile display device to:

display the image captured by the imager, and make a change to a table control mode in which the mobile display device is operated to receive a control command corresponding to the user input for controlling the patient table from the portable user input device and to transmit the control command to a controller configured to control the patient table;

based on the control command for aligning the object with the center of the bore being received via the mobile display device, controlling, by the controller, the patient table so that the patient table is set to automatically align the object with the center of the bore, based on the image captured by the imager;

in response to a user selection for a region of interest (ROI) being received by a touch screen of the mobile display device while the mobile display device is displaying the image captured by the imager, controlling the imager to zoom in the ROI; and controlling the gantry to scan the object to acquire the CT image data of the object.

9. The method of claim 8, wherein the control command includes a control command for laterally setting the patient table to laterally align the object with the center of the bore; and the controlling the patient table further comprises, based on the control command for laterally setting the patient table being obtained via the mobile display device, controlling the patient table so that the patient table is laterally set to laterally align the object with the center of the bore, based on the image captured by the imager.

10. The method of claim 8, wherein the controlling the patient table further comprises controlling the patient table so that the patient table is laterally set to laterally align the object with the center of the bore, based on a position of the object in the image captured by the imager.

11. The method of claim 8, wherein the at least one button includes a hardware portion, and the control command for automatically aligning the object with the center of the bore is obtained via a pressing down of the hardware portion.

12. The method of claim 8, further comprising controlling the mobile display device to display a plurality of information for guiding an acquisition of the CT image data of the object.

13. A non-transitory computer-readable storage medium storing a program comprising instructions which, when executed by a processor, cause the processor to:
- control an imager to capture an image of an object on a patient table for conveying the object to a gantry, wherein the gantry is for scanning the object to acquire computed tomography (CT) image data of the object;
- receive, through at least one button of a portable user input device, a user input for controlling the patient table, the controlling of the patient table comprising automatically aligning the object with a center of a bore of the gantry;
- in response to the portable user input device being connected to a mobile display device connectable to the portable user input device, control the mobile display device to:
  - display the image captured by the imager, and make a change to a table control mode in which the mobile display device is operated to receive a control command corresponding to the user input for controlling the patient table from the portable user input device and to transmit the control command to a controller configured to control the patient table;
- based on the control command for aligning the object with the center of the bore being received via the mobile display device, control the patient table so that the patient table is set to automatically align the object with the center of the bore, based on the image captured by the imager;
- in response to a user selection for a region of interest (ROI) being received by a touch screen of the mobile display device while the mobile display device is displaying the image captured by the imager, control the imager to zoom in the ROI; and
- control the gantry to scan the object to acquire the CT image data of the object.

14. The non-transitory computer-readable storage medium of claim 13, wherein the control command includes a control command for laterally setting the patient table to laterally align the object with the center of the bore; and
the instructions further cause the processor to, based on the control command for laterally setting the patient table being obtained via the mobile display device, control the patient table so that the patient table is laterally set to laterally align the object with the center of the bore, based on the image captured by the imager.

15. The non-transitory computer-readable storage medium of claim 13, wherein the instructions further cause the processor to control the patient table so that the patient table is laterally set to laterally align the object with the center of the bore, based on a position of the object in the image captured by the imager.

16. The non-transitory computer-readable storage medium of claim 13, wherein the at least one button includes a hardware portion, and
the control command for automatically aligning the object with the center of the bore is obtained via a pressing down of the hardware portion.

17. The non-transitory computer-readable storage medium of claim 13, wherein the instructions further cause the processor to control the mobile display device to display a plurality of information for guiding an acquisition of the CT image data of the object.

* * * * *